(12) United States Patent
Zon et al.

(10) Patent No.: US 12,215,351 B2
(45) Date of Patent: Feb. 4, 2025

(54) METHODS FOR INDUCING HEMATOPOIETIC STEM CELL SPECIFICITY

(71) Applicant: THE CHILDREN'S MEDICAL CENTER CORPORATION, Boston, MA (US)

(72) Inventors: Leonard I. Zon, Brookline, MA (US); Joseph Mandelbaum, Boston, MA (US)

(73) Assignee: THE CHILDREN'S MEDICAL CENTER CORPORATION, Boston, MA (US)

( * ) Notice: Subject to any disclaimer, the term of this patent is extended or adjusted under 35 U.S.C. 154(b) by 845 days.

(21) Appl. No.: 16/640,403

(22) PCT Filed: Aug. 21, 2018

(86) PCT No.: PCT/US2018/047242
§ 371 (c)(1),
(2) Date: Feb. 20, 2020

(87) PCT Pub. No.: WO2019/040448
PCT Pub. Date: Feb. 28, 2019

(65) Prior Publication Data
US 2020/0362308 A1   Nov. 19, 2020

Related U.S. Application Data

(60) Provisional application No. 62/548,436, filed on Aug. 22, 2017.

(51) Int. Cl.
| | |
|---|---|
| *C12N 5/0789* | (2010.01) |
| *A61K 31/404* | (2006.01) |
| *A61K 31/426* | (2006.01) |
| *A61K 31/444* | (2006.01) |
| *A61K 31/5513* | (2006.01) |
| *A61K 35/28* | (2015.01) |
| *A61K 35/50* | (2015.01) |
| *A61K 35/545* | (2015.01) |
| *C12N 5/00* | (2006.01) |

(52) U.S. Cl.
CPC .......... *C12N 5/0647* (2013.01); *A61K 31/404* (2013.01); *A61K 31/426* (2013.01); *A61K 31/444* (2013.01); *A61K 31/5513* (2013.01); *A61K 35/50* (2013.01); *A61K 35/545* (2013.01); *C12N 5/0062* (2013.01); *A61K 35/28* (2013.01); *C12N 2501/999* (2013.01)

(58) Field of Classification Search
None
See application file for complete search history.

(56) References Cited

U.S. PATENT DOCUMENTS 9,446,048 B2 *   9/2016   Liu ....................... A61P 35/02
2014/0004082 A1   1/2014   Liu et al.

FOREIGN PATENT DOCUMENTS

| WO | 2007112084 A2 | 10/2007 |
| WO | 2009155041 A2 | 12/2009 |
| WO | 2012125787 A1 | 9/2012 |
| WO | 2018093797 A1 | 5/2018 |

OTHER PUBLICATIONS

Igor I. Slukvin, "Hematopoietic specification from human pluripotent stem cells: current advances and challenges toward de novo generation of hematopoietic stem cells", 2013, Blood, 122(25), pp. 4035-4046. (DOI 10.1182/blood-2013-07-474825) (Year: 2013).*
Slukvin, Hematopoietic specification from human pluripotent stem cells: current advances and challenges toward de novo generation of hematopoietic stem cells (2013), Blood, 122, pp. 4035-4046. (Year: 2013).*
Yvernogeau et al. In vivo generation of haematopoietic stem/progenitor cells from bone marrow-derived haemogenic endothelium (2019) Nature Cell Biology, 21, pp. 1334-1345. (Year: 2019).*
Li et al. Concise Review: A Chemical Approach to Control Cell Fate and Function (2012) Stem Cells, 30, pp. 61-68. (Year: 2012).*
Illendula et al. "Small molecule inhibitor of CBFβ-RUNX binding for RUNX transcription factor driven cancers." EBioMedicine 8: 117-131 (2016).
Mandelbaum. "Modulators of hematopoietic stem cell specification using zebrafish embryo cultures." Thesis, Harvard University: pp. 1-128 Retrieved from the Internet: URL: https://dash.harvard.edu/bitstream/handle/1/40050060/MANDELBAUM-DISSERTATION-2018.pdf?isAllowed=y&sequence=4 (2018).
Bresciani et al. "CBFβ and RUNX1 are required at 2 different steps during the development of hematopoietic stem cells in zebrafish." Blood, The Journal of the American Society of Hematology 124(1): 70-78 (2014).
Chen et al. "Inducible overexpression of RUNX1b/c in human embryonic stem cells blocks early hematopoiesis from mesoderm." Journal of Molecular Cell Biology 9(4): 262-273 (2017).
Cunningham et al. "Identification of benzodiazepine Ro5-3335 as an inhibitor of CBF leukemia through quantitative high throughput screen against RUNX1-CBFβ interaction." Proceedings of the National Academy of Sciences 109(36): 14592-14597 (2012).
Liakhovitskaia et al. "Runx1 is required for progression of CD41+ embryonic precursors into HSCs but not prior to this." Development 141(17): 3319-3323 (2014).
Lie-A-Ling et al. "Regulation of RUNX1 dosage is crucial for efficient blood formation from hemogenic endothelium." Development 145(5): 1-14 (2018).

(Continued)

*Primary Examiner* — Kara D Johnson
*Assistant Examiner* — Maytee Marie Contes De Jesus
(74) *Attorney, Agent, or Firm* — Nixon Peabody LLP; David S. Resnick; Jeanne Jodoin

(57) ABSTRACT

Described herein are methods for inducing HSC specification in a cell. Aspects of the invention relate to contacting a cell with a Runx1-CBFβ inhibitor for a specified period of time, and then removing the inhibitor from the cell. In some embodiments of any of the aspects, HSC specificity is maintained long-term.

12 Claims, 20 Drawing Sheets

(56) References Cited

OTHER PUBLICATIONS

Sroczynska et al. "The differential activities of Runx1 promoters define milestones during embryonic hematopoiesis." Blood, The Journal of the American Society of Hematology 114(26): 5279-5289 (2009).

* cited by examiner

Fold change relative to control shown in each plot

Concentration (μM) →

| | High | Medium | Low |
|---|---|---|---|
| | 10 | 1 | 0.1 |

Ro5-3335: Runx-CBFβ Inhibitor
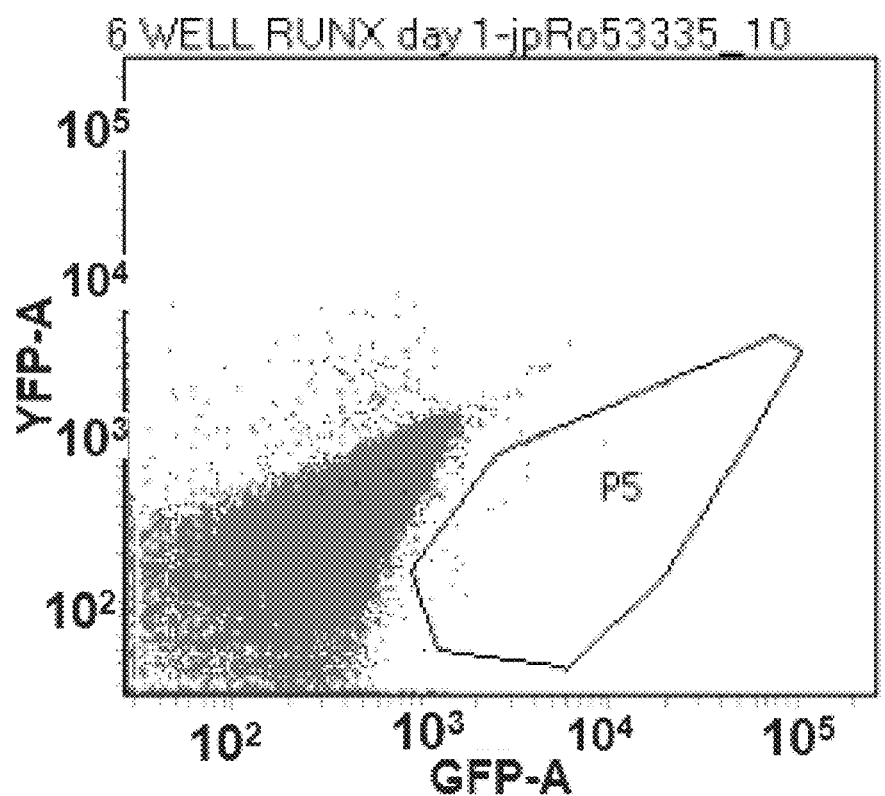
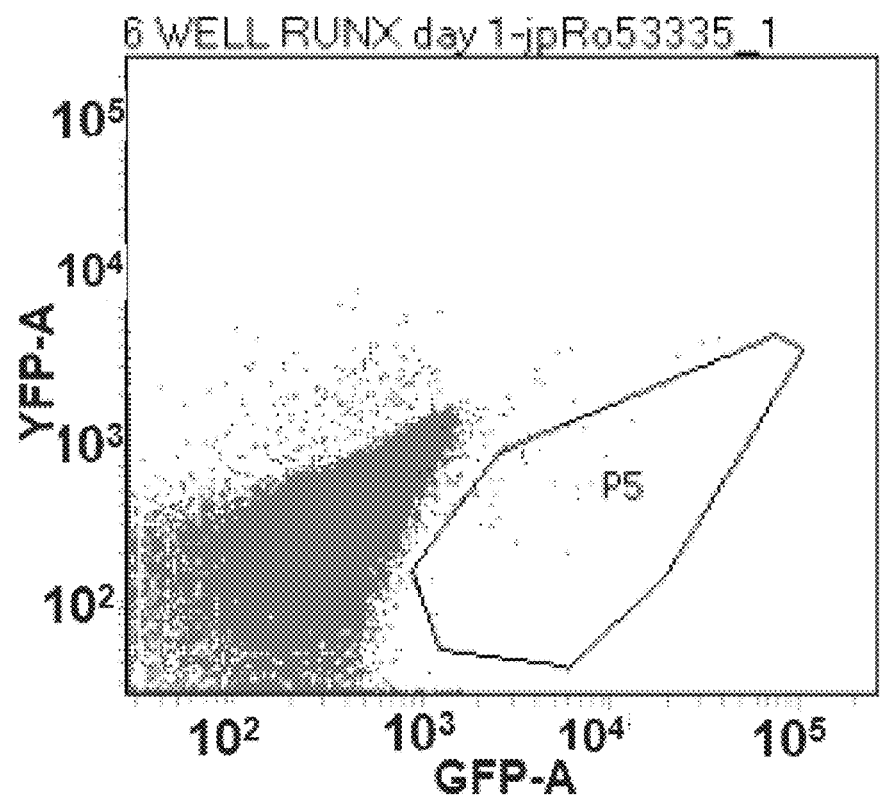
*FIG. 1D, Continued*

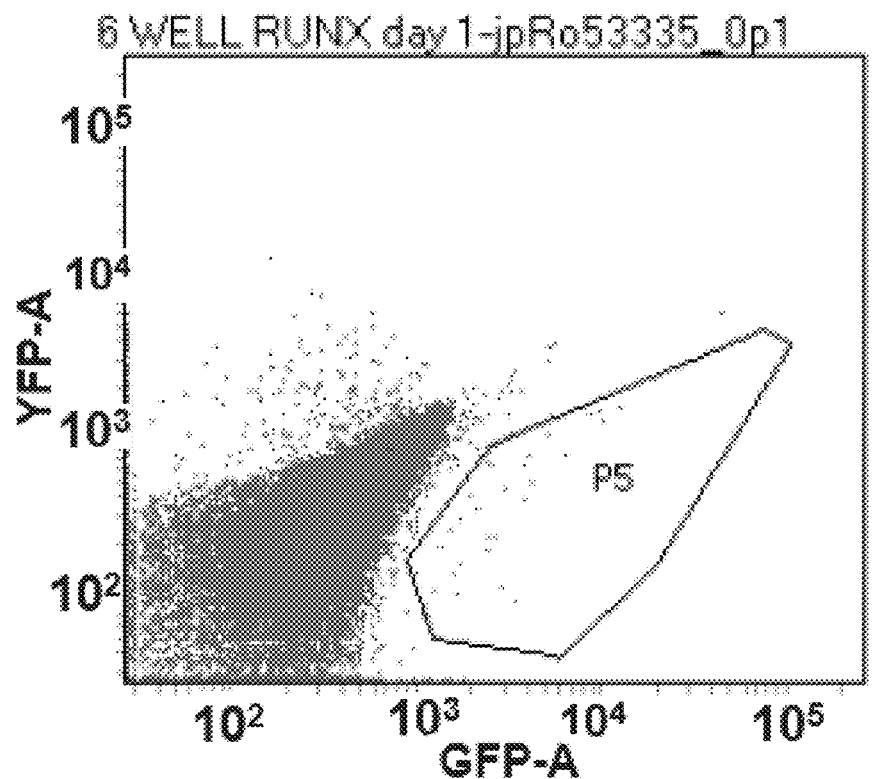
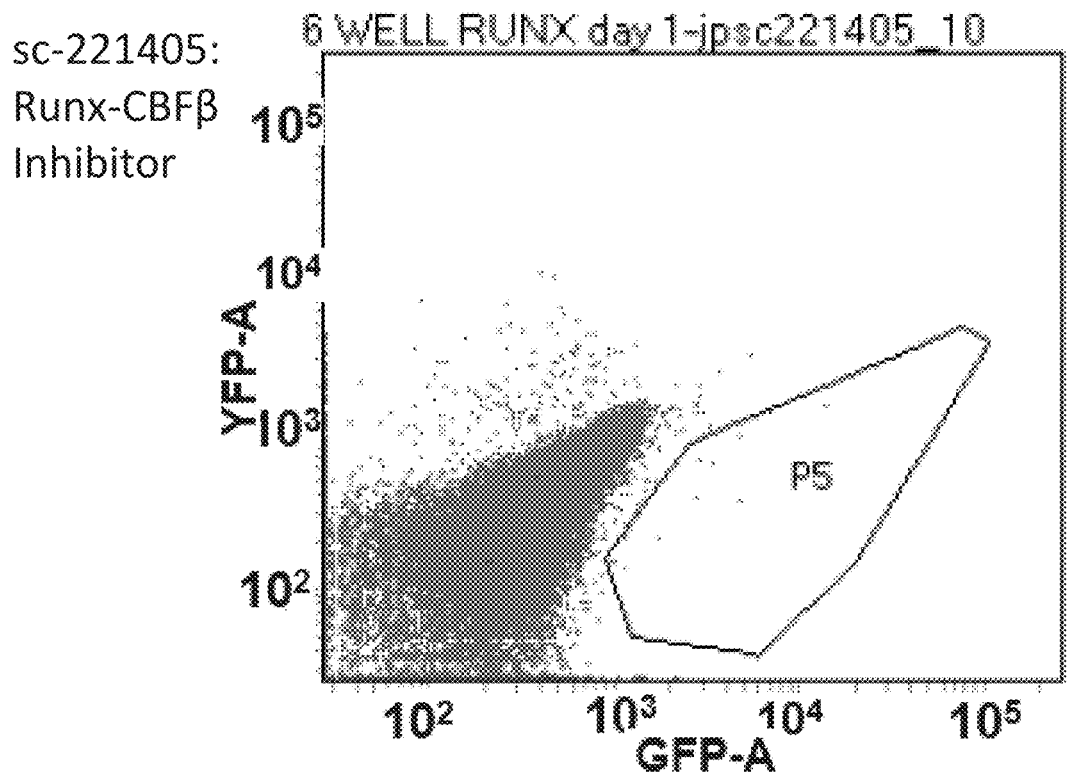
FIG. 1D, Continued

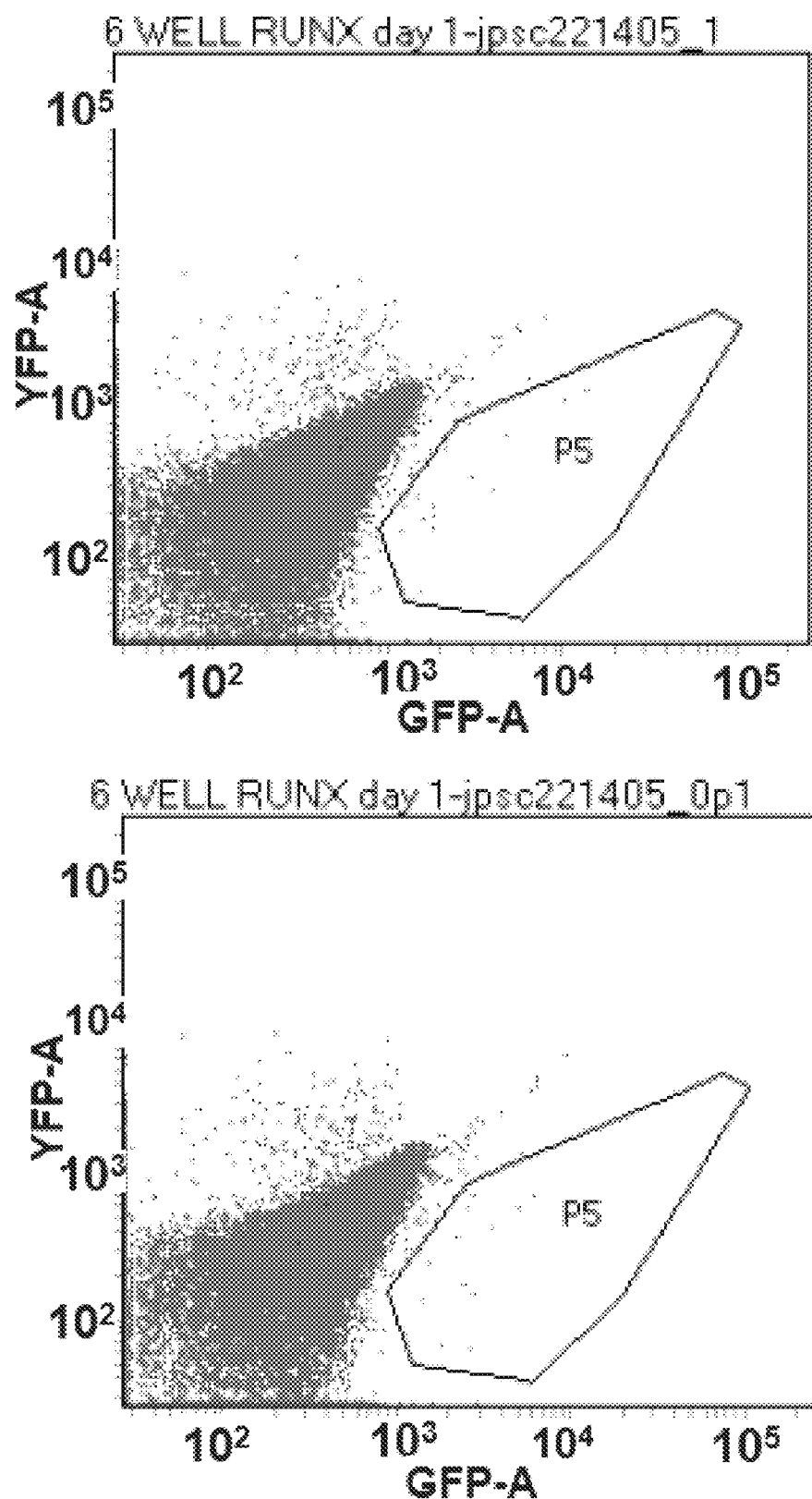
FIG. 1D, Continued

AI-10-49: Runx1 & CBFβ-SMMHC Inhibitor
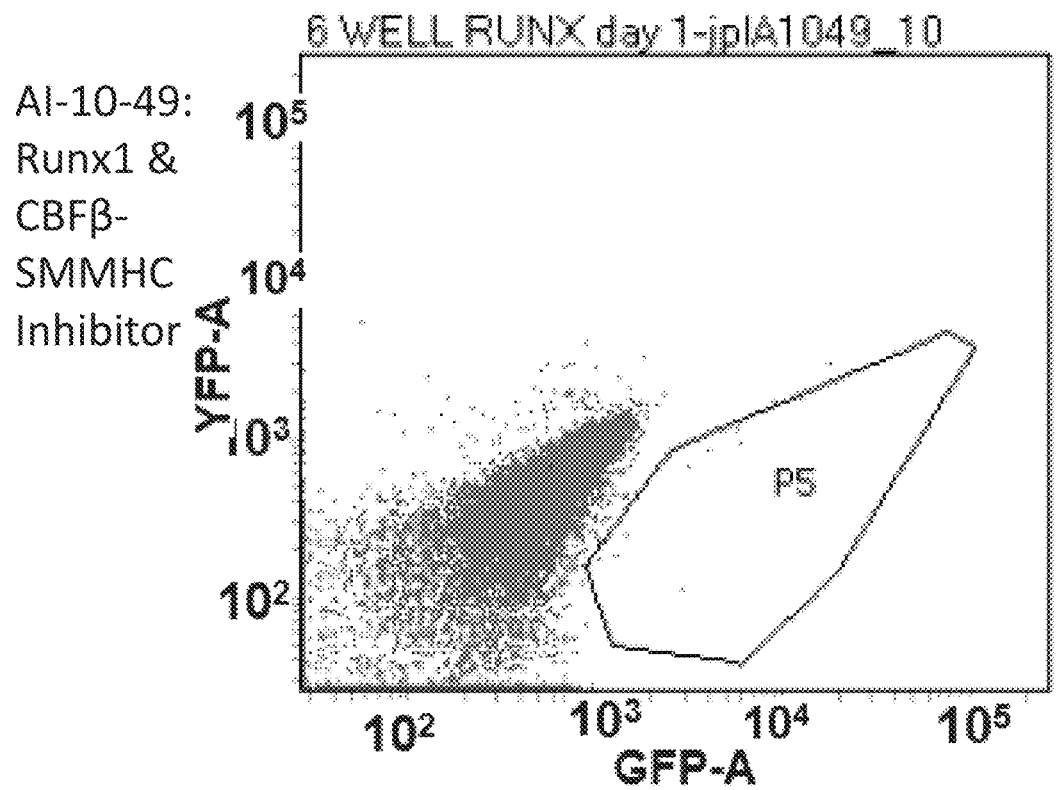
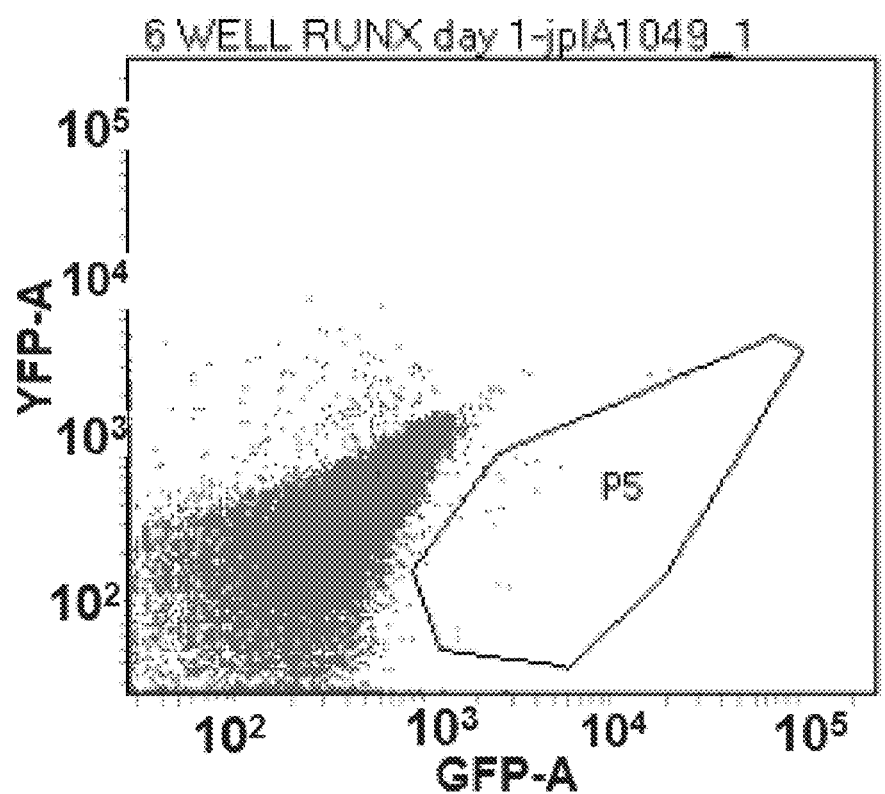
*FIG. 1D, Continued*

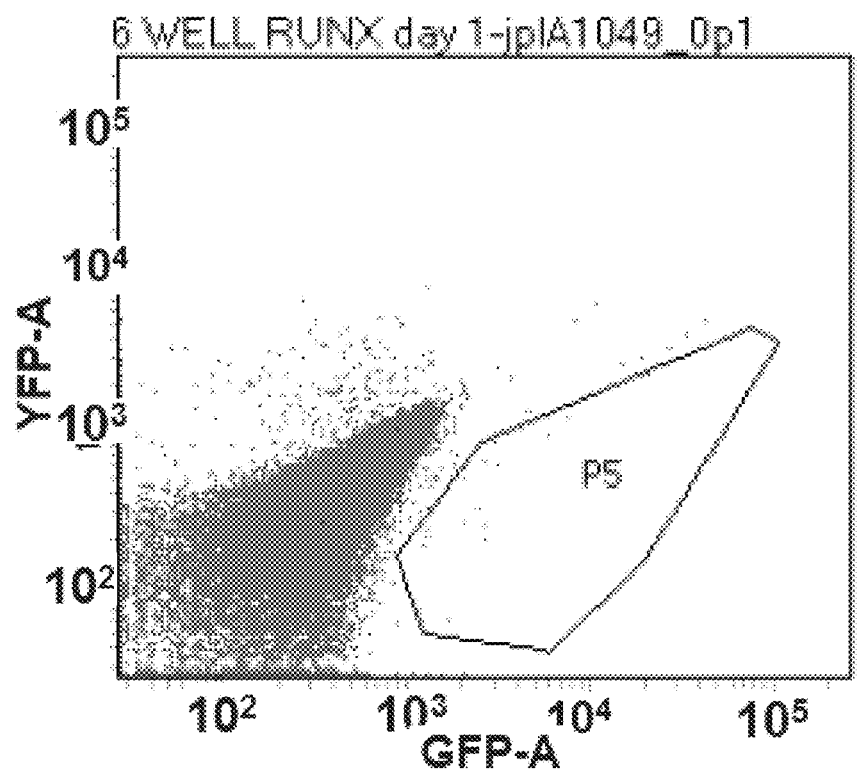
*FIG. 1D, Continued*

METHODS FOR INDUCING HEMATOPOIETIC STEM CELL SPECIFICITY

CROSS REFERENCE TO RELATED APPLICATIONS

This Application is a 35 U.S.C. § 371 National Phase Entry Application of International Application No. PCT/US18/47242, filed Aug. 21, 2018, which designates the U.S. and claims benefit under 35 U.S.C. § 119(e) of U.S. Provisional Application No. 62/548,436 filed Aug. 22, 2017, the contents of which is incorporated herein by reference in their entireties.

GOVERNMENT SUPPORT

This invention was made with Government support under Grant No. RO1 HL048801 awarded by the National Institutes of Health. The Government has certain rights in the invention.

FIELD OF THE INVENTION

The field of the invention relates to methods for inducing hematopoietic stem cell specificity.

BACKGROUND

Hematopoietic stem cells (HSCs) are among the best-characterized and most experimentally tractable tissue-specific stem cells. HSCs reside at the top of hematopoietic hierarchy and give rise to a large repertoire of highly specialized effector cells by differentiating through a succession of increasingly committed downstream progenitor cells. HSCs are the only cells in the hematopoietic system that possess the ability to both differentiate to all blood lineages and to self-renew for life. HSCs derived from embryonic stem cells (ESCs) and induced pluripotent stem cells (iPSC) hold great promise for treating patients lacking an optimally matched donor marrow. Allogeneic and autologous HSC transplantation are routinely used in the treatment of patients with a variety of life-threatening disorders. Despite wide clinical use, HSC transplantation remains a high-risk procedure, with the number of stem cells available for transplantation being the strongest predictor of transplantation success.

SUMMARY

The methods described herein are based, in part, on the discovery that contacting a cell with an inhibitor of Runx1-CBFD induces HSC specificity, and removing of the inhibitor allowed the cells to continue developing normally and maintain long term HSC activity. Accordingly, aspects described herein relate to methods for inducing HSC specification and increasing HSC numbers in a subject.

Accordingly, one aspect of the invention described herein provides a method for inducing hematopoietic stem cell (HSC) specification, the method comprising; (a) contacting a cell for a period of time with an agent selected from the group consisting of Ro5-3335, SU-5402, sc-221405, and AI-10-49; and (b) removing said agent after said period of time, thereby inducing HSC specification.

In one embodiment of any aspect, the period of time of is between 1 and 6 days.

In one embodiment of any aspect, the contacting is in vitro, ex vivo or in vivo.

In one embodiment of any aspect, the concentration of the agent is between 1 µM and 100 µM.

In one embodiment of any aspect, the cell is derived from a dissociated embryo. In one embodiment of any aspect, the dissociated embryo is at least 9 hours post fertilization.

In one embodiment of any aspect, the cell is a mammalian cell. In one embodiment of any aspect, the cell is a human cell. In one embodiment of any aspect, the cell is a nonhuman mammalian cell.

In one embodiment of any aspect, the cell is selected from the group consisting of an hemogenic endothelial (HE) cell, an embryonic cell, an embryonic stem cell (ESC), an embryod bodies, an induced pluripotent stem cell (iPSC), an aorta-gonad-mesonephros (AGM) cell, a placenta stem cell, an adult stem cell, and an amniotic stem cell.

In one embodiment of any aspect, the HSC specification is maintained long-term.

In one embodiment of any aspect, the HSC is transplanted into a recipient.

In one embodiment of any aspect, the HSC cell differentiates into a blood cell.

Another aspect of the invention described herein provides a cell obtained by any of the methods described herein.

Another aspect of the invention described herein provides a method for inducing hematopoietic stem cell (HSC) specification, the method comprising; (a) contacting a cell for a period of time with Ro5-3335; and (b) removing Ro5-3335 after said period of time, thereby inducing HSC.

Another aspect of the invention described herein provides a method for increasing the number of hematopoietic stem cells (HSC) in a subject, the method comprising administering an agent selected from the group consisting of Ro5-3335, SU-5402, sc-221405, and AI-10-49 to a subject.

In one embodiment of any aspect, the number of HSC is increase by at least 150% compared to the number of HSC prior to treatment.

In one embodiment of any aspect, the agent is Ro5-3335.

In one embodiment of any aspect, the agent is formulated for administration to a subject.

In one embodiment of any aspect, the subject is human.

In one embodiment of any aspect, the subject has a decreased blood cell level or is at risk for developing a decreased blood cell level as compared to a control blood cell level.

In one embodiment of any aspect, the method further comprises the step of identifying a subject having a decreased blood cell level or at risk for developing a decreased blood cell level as compared to a control blood cell level prior to administering.

In one embodiment of any aspect, the blood cell level is decreased at least 1% compared to a reference level.

In one embodiment of any aspect, the subject has anemia or blood loss.

In one embodiment of any aspect, the subject is a bone marrow donor.

In one embodiment of any aspect, the subject has depleted bone marrow.

In one embodiment of any aspect, has anemia, hemolysis, leukemia, multiple myeloma, or a thyroid disorder.

Another aspect of the invention described herein provides a method for increasing the number of hematopoietic stem cells (HSC) in a subject, the method comprising:
  identifying a subject having a decreased blood cell level, or at risk for developing a decreased blood cell level as compared to a control blood cell level; and administering an agent selected from the group consisting of Ro5-3335, SU-5402, sc-221405, and AI-10-49 to the subject.

Another aspect of the invention described herein provides a kit for inducing hematopoietic stem cell (HSC) specification, the method comprising; (a) an agent selected from the group consisting of Ro5-3335, SU-5402, sc-221405, and AI-10-49; and (b) a positive control.

Another aspect of the invention described herein provides a kit for increasing the number of hematopoietic stem cells (HSC) in a subject, the method comprising: (a) an agent formulated for administration to a subject selected from the group consisting of Ro5-3335, SU-5402, sc-221405, and AI-10-49; and (b) a positive control.

Definitions

The term "HSC inducing agent," as used herein, refers to a developmental potential altering agent, as that term is defined herein, such as a small molecule, which contributes to the reprogramming of a cell, e.g. a somatic cell, to the HSC state. An HSC inducing agent can be, for example, Ro5-3335, SU-5402, sc-221405, AI-10-49.

The term "multipotent" when used in reference to a "multipotent cell" refers to a cell that has the developmental potential to differentiate into cells of one or more germ layers, but not all three. Thus, a multipotent cell can also be termed a "partially differentiated cell." Multipotent cells are well known in the art, and examples of multipotent cells include adult stem cells, such as for example, hematopoietic stem cells and neural stem cells. "Multipotent" indicates that a cell may form many types of cells in a given lineage, but not cells of other lineages. For example, a multipotent hematopoietic cell can form all of the many different types of blood cells (red, white, platelets, etc. . . . ), but it cannot form neurons. Accordingly, the term "multipotency" refers to a state of a cell with a degree of developmental potential that is less than totipotent and pluripotent.

The terms "stem cell" or "undifferentiated cell" as used herein, refer to a cell in an undifferentiated or partially differentiated state that has the property of self-renewal and has the developmental potential to differentiate into multiple cell types, without a specific implied meaning regarding developmental potential (i.e., totipotent, pluripotent, multipotent, etc.). A stem cell is capable of proliferation and giving rise to more such stem cells while maintaining its developmental potential. In theory, self-renewal can occur by either of two major mechanisms. Stem cells can divide asymmetrically, which is known as obligatory asymmetrical differentiation, with one daughter cell retaining the developmental potential of the parent stem cell and the other daughter cell expressing some distinct other specific function, phenotype and/or developmental potential from the parent cell. The daughter cells themselves can be induced to proliferate and produce progeny that subsequently differentiate into one or more mature cell types, while also retaining one or more cells with parental developmental potential. A differentiated cell may derive from a multipotent cell, which itself is derived from a multipotent cell, and so on. While each of these multipotent cells can be considered stem cells, the range of cell types each such stem cell can give rise to, i.e., their developmental potential, can vary considerably. Alternatively, some of the stem cells in a population can divide symmetrically into two stem cells, known as stochastic differentiation, thus maintaining some stem cells in the population as a whole, while other cells in the population give rise to differentiated progeny only. Accordingly, the term "stem cell" refers to any subset of cells that have the developmental potential, under particular circumstances, to differentiate to a more specialized or differentiated phenotype, and which retain the capacity, under certain circumstances, to proliferate without substantially differentiating. In some embodiments, the term stem cell refers generally to a naturally occurring parent cell whose descendants (progeny cells) specialize, often in different directions, by differentiation, e.g., by acquiring completely individual characters, as occurs in progressive diversification of embryonic cells and tissues. Some differentiated cells also have the capacity to give rise to cells of greater developmental potential. Such capacity can be natural or can be induced artificially upon treatment with various factors. Cells that begin as stem cells can proceed toward a differentiated phenotype, but then can be induced to "reverse" and re-express the stem cell phenotype, a term often referred to as "dedifferentiation" or "reprogramming" or "retrodifferentiation" by persons of ordinary skill in the art, and as used herein.

In the context of cell ontogeny, the term "differentiate", or "differentiating" is a relative term that refers to a developmental process by which a cell has progressed further down a developmental pathway than its immediate precursor cell. Thus in some embodiments, a reprogrammed cell as the term is defined herein, can differentiate to a lineage-restricted precursor cell, which in turn can differentiate into other types of precursor cells further down the pathway (such as a blood cell, for example), and then to end-stage differentiated cells, which play a characteristic role in a certain tissue type, and may or may not retain the capacity to proliferate further.

The term "expression" refers to the cellular processes involved in producing RNA and proteins and as appropriate, secreting proteins, including where applicable, but not limited to, for example, transcription, translation, folding, modification and processing. "Expression products" include RNA transcribed from a gene, and polypeptides obtained by translation of mRNA transcribed from a gene.

The term "agent" as used herein means any compound or substance such as, but not limited to, a small molecule, nucleic acid, polypeptide, peptide, drug, ion, etc. An "agent" can be any chemical, entity or moiety, including without limitation synthetic and naturally-occurring proteinaceous and non-proteinaceous entities. In some embodiments, an agent is nucleic acid, nucleic acid analogues, proteins, antibodies, peptides, aptamers, oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof etc. In certain embodiments, agents are small molecule having a chemical moiety. For example, chemical moieties included unsubstituted or substituted alkyl, aromatic, or heterocyclyl moieties including macrolides, leptomycins and related natural products or analogues thereof. Compounds can be known to have a desired activity and/or property, or can be selected from a library of diverse compounds.

The agent can be a molecule from one or more chemical classes, e.g., organic molecules, which may include organometallic molecules, inorganic molecules, genetic sequences, etc. Agents may also be fusion proteins from one or more proteins, chimeric proteins (for example domain switching or homologous recombination of functionally significant regions of related or different molecules), synthetic proteins or other protein variations including substitutions, deletions, insertion and other variants.

As used herein, the term "small molecule" refers to a chemical agent which can include, but is not limited to, a peptide, a peptidomimetic, an amino acid, an amino acid analog, a polynucleotide, a polynucleotide analog, an aptamer, a nucleotide, a nucleotide analog, an organic or inorganic compound (e.g., including heterorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

The term "isolated cell" as used herein refers to a cell that has been removed from an organism in which it was originally found, or a descendant of such a cell. Optionally the cell has been cultured in vitro, e.g., in the presence of other cells. Optionally, the cell is later introduced into a second organism or re-introduced into the organism from which it (or the cell or population of cells from which it descended) was isolated.

The term "isolated population" with respect to an isolated population of cells as used herein refers to a population of cells that has been removed and separated from a mixed or heterogeneous population of cells. In some embodiments, an isolated population is a "substantially pure" population of cells as compared to the heterogeneous population from which the cells were isolated or enriched. In some embodiments, the isolated population is an isolated population of multipotent cells which comprise a substantially pure population of multipotent cells as compared to a heterogeneous population of somatic cells from which the multipotent cells were derived.

The term "contacting" or "contact" as used herein in connection with contacting a cell with one or more agents, includes subjecting a cell to a culture medium which comprises one or more agent at least one time, or a plurality of times, or to a method whereby such agents are forced to contact a cell at least one time, or a plurality of times. Where such a cell is in vivo, contacting the cell with agent includes administering the agent in a composition, such as a pharmaceutical composition, to a subject via an appropriate administration route, such that the compound contacts the cell in vivo.

The term "gene" used herein can be a genomic gene comprising transcriptional and/or translational regulatory sequences and/or a coding region and/or non-translated sequences (e.g., introns, 5'- and 3'-untranslated sequences and regulatory sequences). The coding region of a gene can be a nucleotide sequence coding for an amino acid sequence or a functional RNA, such as tRNA, rRNA, catalytic RNA, siRNA, miRNA and antisense RNA. A gene can also be an mRNA or cDNA corresponding to the coding regions (e.g. exons and miRNA) optionally comprising 5'- or 3' untranslated sequences linked thereto. A gene can also be an amplified nucleic acid molecule produced in vitro comprising all or a part of the coding region and/or 5'- or 3'-untranslated sequences linked thereto. The term "gene product(s)" as used herein refers to include RNA transcribed from a gene, or a polypeptide encoded by a gene or translated from RNA.

The terms "lower", "reduced", "reduction" or "decrease", or "inhibit" are all used herein generally to mean a decrease by a statistically significant amount. However, for avoidance of doubt, "lower", "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e. absent level as compared to a reference sample), or any decrease between 10-100% as compared to a reference level. When "decrease" or "inhibition" is used in the context of the level of expression or activity of a gene or a protein, it refers to a reduction in protein or nucleic acid level or activity in a cell, a cell extract, or a cell supernatant. For example, such a decrease may be due to reduced RNA stability, transcription, or translation, increased protein degradation, or a small molecule inhibitor. In the context of a marker, a "decrease" is a statistically significant increase in such level.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker, an "increase" is a statistically significant increase in such level.

As used herein, a "reference level" refers to a normal, otherwise unaffected cell population or tissue (e.g., a biological sample obtained from a healthy subject, or a biological sample obtained from the subject at a prior time point, e.g., a biological sample obtained from a patient prior to administration of an agent described herein).

As used herein, an "appropriate control" refers to an untreated, otherwise identical cell or population (e.g., a patient who was not administered an agent described herein, as compared to a non-control cell).

The term "inhibitor" and "antagonist" refers to an agent that inhibits expression of a polypeptide or polynucleotide, or binds to, partially or totally blocks stimulation, decreases, prevents, delays activation, inactivates, desensitizes, or down regulates the activity of the polypeptide or the polynucleotide. Inhibitors are agents that, for example inhibit expression (e.g., translation, post-translational processing, stability, degradation, or nuclear or cytoplasmic localization of a polypeptide, or transcription, post transcriptional processing, stability or degradation of a polynucleotide or bind to, partially or totally block stimulation, DNA binding, transcription factor activity or enzymatic activity, decrease, prevent, delay activation, inactivate, desensitize, or down regulate the activity of a polypeptide or polynucleotide). An inhibitor can act directly or indirectly. Inhibition is achieved when the activity value of a polypeptide or polynucleotide is about at least 10% less, at least 20% less, at least 30% less, at least 40% less, at least 50% less, at least 60% less, at least 70% less, at least 80% less, at least 90% less, or absent or undetectable in comparison to a reference or control level in the absence of the inhibitor.

The terms "significantly different than", "statistically significant", and similar phrases refer to comparisons between data or other measurements, wherein the differences between two compared individuals or groups are evidently or reasonably different to the trained observer, or statistically significant (if the phrase includes the term "statistically" or if there is some indication of statistical test, such as a p-value, or if the data, when analyzed, produce a statistical difference by standard statistical tests known in the art).

As used herein, a "subject" means a human or animal. Usually the animal is a vertebrate such as a primate, rodent, domestic animal or game animal. Primates include, for example, chimpanzees, cynomologous monkeys, spider monkeys, and macaques, e.g., Rhesus. Rodents include, for example, mice, rats, woodchucks, ferrets, rabbits and hamsters. Domestic and game animals include, for example, cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of disease e.g., decreased blood cell level. A subject can be male or female.

A subject can be one who has been previously diagnosed with or identified as suffering from or having a disease or disorder in need of treatment (e.g., decreased blood cell level, and in need of increased HSCs) or one or more complications related to such a disease or disorder, and optionally, have already undergone treatment for the disease or disorder or the one or more complications related to the disease or disorder. Alternatively, a subject can also be one who has not been previously diagnosed as having such disease or disorder (e.g., decreased blood cell level) or related complications. For example, a subject can be one who exhibits one or more risk factors for the disease or disorder or one or more complications related to the disease or disorder or a subject who does not exhibit risk factors.

The term "effective amount" is used interchangeably with the terms "sufficient amount" and "therapeutically effective amount" and refers to the amount of at least one agent, e.g., Ro5-3335, at dosages and for periods of time necessary to achieve the desired therapeutic result, e.g., to increase HSC in a subject. For example, an effective amount using the methods as disclosed herein would be considered as the amount sufficient to increase HSC by at least 1%, at least 5%, at least 10%, at least 20%, at least 30%, at least 40%, at least 50%, at least 60%, at least 70%, at least 90%, at least 100%, at least 110%, at least 120%, at least 130%, at least 140%, or at least 150% as measured by any standard technique. In one embodiment, an effective amount using the methods as disclosed herein would be considered as the amount sufficient to increase HSC by at least 150%. Accordingly, the term "effective amount" or "therapeutically effective amount" as used herein refers to the amount of therapeutic agent (e.g. at least one Runx1-CBFD inhibitor) of pharmaceutical composition to increase HSC specificity. The dosage administered, as single or multiple doses, to an individual will vary depending upon a variety of factors, including pharmacokinetic properties of the agent, the route of administration, conditions and characteristics (sex, age, body weight, health, size) of subjects, extent of symptoms, concurrent treatments, frequency of treatment and the effect desired. A therapeutically effective amount is also one in which any toxic or detrimental effects of the agent are outweighed by the therapeutically beneficial effects. The effective amount in each individual case can be determined empirically by a skilled artisan according to established methods in the art and without undue experimentation.

The "pharmaceutical administration" and "pharmaceutically acceptable" are employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" as used herein means a pharmaceutically acceptable material, composition or vehicle, such as a liquid or solid filler, diluent, excipient, solvent or encapsulating material, involved in carrying or transporting the agents from one organ, or portion of the body, to another organ, or portion of the body. Each carrier must be "acceptable" in the sense of being compatible with the other ingredients of the formulation, for example the carrier does not decrease the impact of the agent on the treatment. In one embodiment, a carrier is pharmaceutically inert. The terms "physiologically tolerable carriers" and "biocompatible delivery vehicles" are used interchangeably.

The term "optional" or "optionally" means that the subsequent described event, circumstance or substituent may or may not occur, and that the description includes instances where the event or circumstance occurs and instances where it does not.

As used herein, the term "comprising" means that other elements can also be present in addition to the defined elements presented. The use of "comprising" indicates inclusion rather than limitation. The term "consisting of" refers to compositions, methods, and respective components thereof as described herein, which are exclusive of any element not recited in that description of the embodiment. The term permits the presence of elements that do not materially affect the basic and novel or functional characteristic(s) of that embodiment of the invention. As used herein the term "consisting essentially of" refers to those elements required for a given embodiment. The term permits the presence of elements that do not materially affect the basic and novel or functional characteristic(s) of that embodiment of the invention.

The term "interferes" or "blocks" means that the process or activity is prevented from continuing or being carried out properly. Used herein, it described that the endogenous function of the protein is altered in a way that is negative to the outcome of a gene or gene product (e.g., protein). This action can be direct or indirect to said gene or gene product.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

BRIEF DESCRIPTION OF THE DRAWINGS

(FIG. 1A) Schematic of a high-throughput image-based chemical screening assay involving Runx1:GFP transgenic zebrafish embryos dissociated at 24 hpf. Resulting cells were plated into 384-well plates with chemicals in duplicate. After 2 days, the 384-well plates were imaged using a Yokogawa CellVoyager™ 7000 and analyzed. (FIGS. 1B and 1C) The runx1-CBFβ inhibitor Ro5-3335 increased GFP signal in the embryo cultures and was confirmed by a dose response curve. (FIG. 1D) In vitro dose responses of runx1-CBFβ inhibitors by FACS. Runx1: GFP+ fold change relative to DMSO control is shown.

(FIG. 2A) Runx1:GFP zebrafish embryos were treated at 24-30 hpf with 5 μM Ro5-3335 and then the CHT region was imaged. (FIG. 2B-2C) Ro5-3335 increased Runx1:GFP positive cells in the CHT at 54 hpf *P<0.05 by unpaired one-tailed t-test. Each dot on graph represents the CHT of an individual embryo scored blindly for each condition, and combined for the Runx1:GFP population (FIG. 2C). (FIG. 2D-2F) Ro5-3335 increased Runx1:GFP positive cells in the CHT when treating embryos for longer timepoints: at 24-48 hpf (FIG. 2D) or 24-54 hpf (FIG. 2E) and imaging at 54 hpf, or treating at 24-72 hpf and imaging at 72 hpf (FIG. 2F). hpf, hours post fertilization. CHT, caudal hematopoietic tissue.

(FIG. 3A) Schematic of transplantation protocol. Whole kidney marrows of recipients were analyzed approximately three months post-transplant. (FIG. 3B) Representative FACS plots of whole kidney marrows from individual recipients. (FIG. 3C) Ro5-3335 treatment increased the engraftment of the GFP+ population. *P<0.05 by unpaired one-tailed t-test.

(FIG. 4A) Human hematopoietic differentiation through hemogenic endothelium (HE). Cells undergoing EHT were analyzed at day 6 for HSPC markers. RUJNX1c reporter cells were analyzed at day 4. (FIG. 4B) Representative FACS plots of hemogenic endothelium cells sorted at day 6 of EHT. (FIG. 4C) Ro5-3335 treatment increased hematopoietic induction of CD34+CD45+ cells at day 6 of HT. (FIG. 4D) Representative FACS plots of RUNX1c reporter activity showed a Ro5-3335 dose-dependent effect. (FIG. 4E) Ro5-3335 treatment increased RUNX1c+24 reporter positivity of hemogenic endothelium cells at day 4 of EHT.

(FIG. 5A) In one mouse, the chimerism of human CD45+ cells in the bone marrow at 6 weeks post-transplant was 0.017% from Ro5-3335 treated cells. There was no engraftment from DMSO treated cells in two mice analyzed. (FIG. 5B) Although the chimerism was low of the mouse that received Ro5-3335 treated cells, there was a clear population expressing the myeloid marker CD33. B- and T-cells, marked by CD19 and CD3 respectively, were not detected.

(FIG. 6A) HSC specification strategy using transient CBFβ chemical inhibition. Washing off the inhibitor would allow the cells to continue developing normally and maintain long-term HSC activity after transplant. (FIG. 6B) Activation of the Runx1+23 enhancer serves as a marker of HSPCs. In hemogenic endothelium cells, which are in a CBFβ repressed state, the enhancer is on to increase runx1 expression. As HSPCs differentiate, increasing CBFβ activity suppresses the enhancer activity. The enhancer becomes activated and is responsive upon runx1-CBFβ inhibition to maintain a stem cell state.

DETAILED DESCRIPTION

Figure 1A:
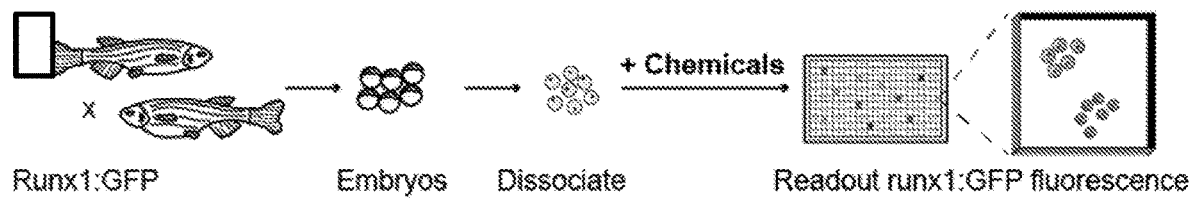
FIGS. 1A-1D show chemical genetic screen identifies modulators of HSPCs.
Figure 1B:
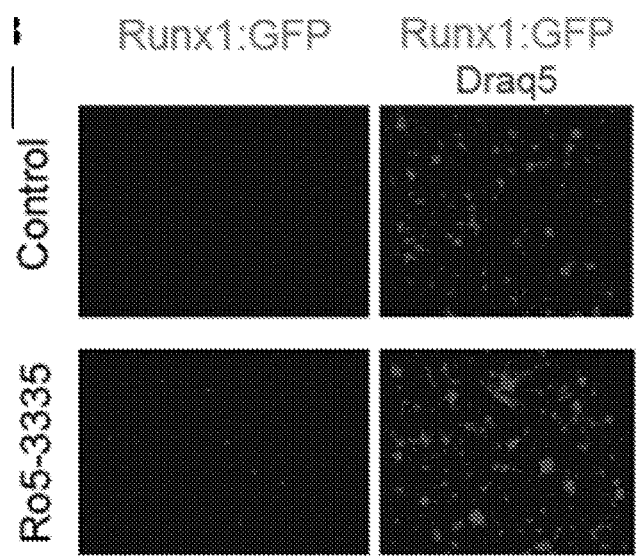

The invention described herein relates to, in part, the discovery that HSC specification can be induced by contacting the cells with a Ro5-3335, a small molecule inhibitor of Runx1-CBFD, for an extended period of time, followed by the removal of the small molecule. It was found that this contact with, and subsequent removal of, Ro5-3335 induced cells to adapt a HSC specificity, and that the specificity was maintained for an extended period of time. Accordingly, aspects described herein relate to methods for inducing a cell to adopt HSC specificity.

Hematopoietic Stem Cells

Hematopoietic tissues contain cells with long-term and short-term regeneration capacities, and committed multipotent, oligopotent, and unipotent progenitors. Endogenous HSCs can be can be found in a variety of tissue sources, such as the bone marrow of adults, which includes femurs, hip, ribs, sternum, and other bones, as well as umbilical cord blood and placenta, and mobilized peripheral blood. Endogenous HSCs can be obtained directly by removal from, for example, the hip, using a needle and syringe, or from the blood following pre-treatment with cytokines, such as G-CSF (granulocyte colony-stimulating factors), that induce cells to be released from the bone marrow compartment. However, such methods yield varying amounts of HSCs, which are oftentimes not enough for use in treatment options.

Accordingly, "HSCs," as the terms are used herein, encompass all multipotent cells capable of differentiating into all the blood or immune cell types of the hematopoietic system, including, but not limited to, myeloid cells (monocytes and macrophages, neutrophils, basophils, eosinophils, erythrocytes, megakaryocytes/platelets, dendritic cells), and lymphoid lineages (T-cells, B-cells, NKT-cells, NK-cells), and which have multi-lineage hematopoietic differentiation potential and sustained self-renewal activity.

Induction of HSC Specification

One aspect of the invention relates to a method for inducing HSC specification, comprising; contacting a cell for a period of time with an agent selected from the group consisting of Ro5-3335, SU-5402, sc-221405, and AI-10-49; and removing said agent after said period of time, thereby inducing HSC. In doing so, a cell is sequestered in a HSC-specified state.

In one embodiment, the method comprises contacting a cell for a period of time with a broad-class Runx1-CFBβ inhibitor, and removing said agent after said period of time, thereby inducing HSC.

Another aspect of the invention relates to a method for inducing HSC specification, comprising; contacting a cell for a period of time with Ro5-3335; and removing Ro5-3335 after said period of time, thereby inducing HSC. In doing so, a cell is sequestered in a HSC-specified state.

Using standard techniques known in the art, one can assess whether HSC specificity has been induced following contact of a cell with an agent described herein, for example, by using flow cytometry to determine if a HSC-specific marker is present or absent. Non-limiting examples of markers specific for human HSC-specificity include cKit/CD117-positive, CD34-positive, CD59-positive, CD38-negative, and Thy1/CD90-positive. HSC lack expression of mature blood cell markers and are thus called Lin-negative.

In one embodiment of all aspects, a cell is contacted with Ro5-3335. Ro5-3335 is a small molecule inhibitor of CBFβ and has been shown to attenuate hematopoiesis. The chemical name for Ro5-3335 is 7-Chloro-1,3-dihydro-5-(1H-pyrrol-2-yl)-2H-1,4-benzodiazepin-2-one, and is commercially available and can be purchased, for example from Tocris, Minneapolis, MN.

Ro5-3335 is a cell-permeable benzodiazepine that suppresses CBFα/Runx1-CBFβ transactivation activity via direct bindings to both subunits of the heterodimeric transcription factor complex. Ro5-3335 has been shown to inhibit oncogenic fusion CBFβ-MYH11-, TEL-RUNX1-, and RUNX1-ETO-dependent leukemia cells proliferation in vitro. Ro5-3335 more effectively reduces peripheral blood c-kit+ population than other similar inhibitors, for example, Cytarabine in a murine Cbfb-MYH11 leukemia model in vivo. Compared to CBFβ-Runx1 Inhibitor I, Ro5-3335 modulates the Runx1-CBFβ heterodimer formation without completely disrupting the subunits interaction.

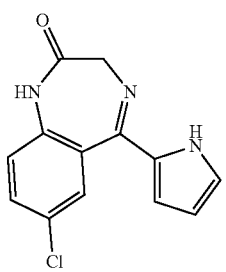

Ro5-3335

In one embodiment of all aspects, a cell is contacted with SU-5402. SU-5402 is a small molecule inhibitor of VEGR2, FGFR1, and PDGFRβ in a cell-type dependent manner. The chemical name for SU-5402 is 2-[(1,2-Dihydro-2-oxo-3H-indol-3-ylidene)methyl]-4-methyl-1H-pyrrole-3-propanoic acid, and is commercially available and can be purchased, for example from Sigma Aldrich, St. Louis, MO.

SU-5402 inhibits VEGF-, FGF-, PDGF-dependent cell proliferation. In addition, SU5416 selectively inhibits VEGF-driven mitogenesis in a dose-dependent manner. In nasopharyngeal epithelial cells, SU-5402 attenuates LMP1-mediated aerobic glycolysis, cellular transformation, cell migration, and invasion. In mouse C3H10T1/2 cells, SU-5402 diminishes the effect of FGF23 on cell differentiation. In mice, SU5416 inhibits subcutaneous growth of a panel of tumor cell lines by inhibiting the angiogenic process associated with tumor growth.

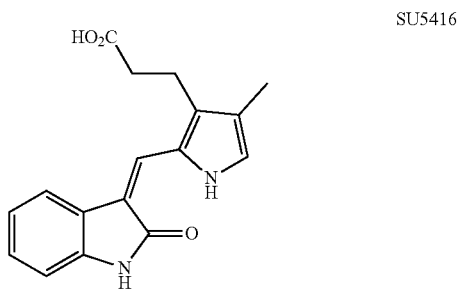 [SMILES: Cc1c[nH]c(/C=C2\C(=O)Nc3ccccc32)c1CCC(=O)O]

SU5416

In one embodiment of all aspects, a cell is contacted with sc-221405. Sc-221405 is a small molecule inhibitor of CBFβ. The chemical name for sc-221405 is 5-Ethyl-4-(4′-methoxyphenyl)-thiazolyl-2-amine; 5-ethyl-4-(4-methoxyphenyl)-1,3-thiazol-2-amine, and is commercially available and can be purchased, for example from Santa Cruz Biotechnology, Dallas, TX.

Sc-221405 is a cell-permeable thiazolyl compound that binds to PEBP20 (CBFβ) and allosterically disrupts CBFα/Runx1 binding to PEBP20 (CBFβ). Cellular studies using sc-221405 indicate a good correlation between the inhibitor's antiproliferative activity and the Runx1 expression level in the target cells.

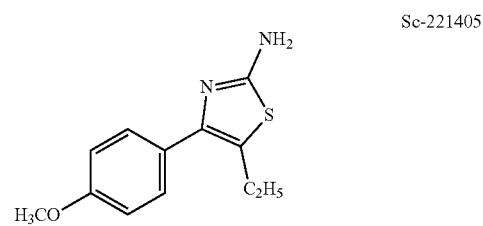 [SMILES: CCc1sc(N)nc1-c1ccc(OC)cc1]

Sc-221405

In one embodiment of all aspects, a cell is contacted with AI-10-49. AI-10-49 is a small molecule inhibitor of CBFβ. The chemical name for AI-10-49 is 2,2'-[oxybis(2,1-ethanediyloxy-5,2-pyridinediyl)]bis[6-(trifluoromethoxy)-1H-benzimidazole, and is commercially available and can be purchased, for example from Cayman Chemical, Ann Arbor, MI.

AI-10-49 is an inhibitor that binds the transcription factor fusion CBFβ-SMMHC (core binding factor β and smooth muscle myosin heavy chain) and blocks its binding to the transcription factor RUNX1. It restores RUNX1 transcriptional activity, displays favorable pharmacokinetics, and delays leukemia progression in mice. AI-10-49 allosterically binds to CBFβ-SMMHC and disrupts protein-protein interaction between CBFβ-SMMHC and tumor suppressor RUNX1. This inhibitor is under development as an anti-leukemic drug.

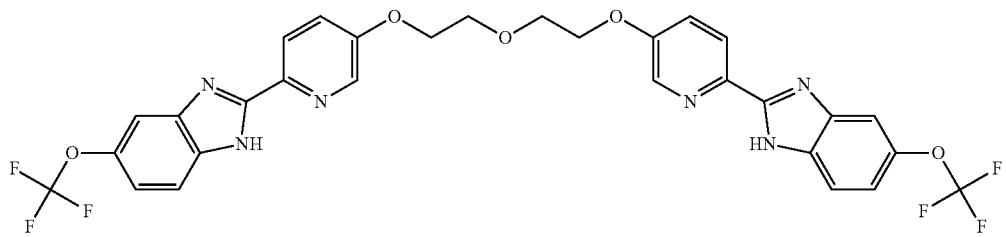

AI-10-49

In one embodiment of all aspects, the cell is a hemogenic endothelial (HE) cell, an embryonic cell, an embryonic stem cell (ESC), an embryoid body, an induced pluripotent stem cell (iPSC), an aorta-gonad-mesonephros (AGM) cell, a placenta stem cell, an adult stem cell, or an amniotic stem cell. In one embodiment, the stem cell is not derived from an embryo. These cells possess the developmental potential to become a HSC. As used herein, the terms "developmental potential" or refer to the total of all developmental cell fates or cell types that can be achieved by a given cell upon differentiation.

In one embodiment, the cell to be contacted by the agent is derived from a dissociated embryo. In one embodiment, the cell to be contacted by the agent is not derived from a dissociated embryo. In one embodiment of all aspects, the embryo is at least 9 hours post fertilization. In one embodiment of all aspects, the embryo is at least 9, at least 10, at least 11, at least 12, at least 13, at least 14, at least 15, at least 16, at least 17, at least 18, at least 19, at least 20, at least 21, at least 22, at least 23, or at least 24 hours post fertilization. One skilled in the art will be able to dissociate an embryo and isolate a single cell, or population thereof. An example publication wherein this skill is taught is Horstick E J, Gibbs E M, Li X, Davidson A E, and Dowling J J. J. Vis. Exp. 2013; (81): 50259, which is incorporated herein by reference in its entirety.

In one embodiment of all aspects, the cell is contacted by the agent for a period of time between 1 and 6 days (inclusive) prior to removing the agent from the cell. In one embodiment, the cell is contacted by the agent for less than 1 day. In one embodiment, the cell is contacted by the agent for at least 1 day, for at least 2 days, for at least 3 days, for at least 4 days, for at least 5 days, or for at least 6 days prior to removing the agent for the cell. Contacting can occur in a media used for cell culturing, e.g., the agent can be added directly to the culturing media, or can occur in a buffer compatible with cell growth and maintenance.

In one embodiment, contacting is continuous, i.e., the agent is maintained on the cells at a constant concentration over the given period of time. In another embodiment, contacting is not continuous, i.e., the agent is not maintained on the cells at a constant concentration over the given period of time. For example, the concentration of the agent can range from 0 to the desired concentration throughout the given period of time.

In one embodiment of all aspects, the concentration of the agent contacting the cell is between 1 µM and 100 µM (inclusive). In one embodiment of all aspects, the concentration of the agent contacting the cell is at least 1 µM, at least 2 µM, at least 3 µM, at least 4 µM, at least 5 µM, at least 6 µM, at least 7 µM, at least 8 µM, at least 9 µM, at least 10 µM, at least 11 µM, at least 12 µM, at least 13 µM, at least 14 µM, at least 15 µM, at least 16 µM, at least 17 µM, at least 18 µM, at least 19 µM, at least 20 µM, at least 21 µM, at least 22 µM, at least 23 µM, at least 24 µM, at least 25 µM, at least 26 µM, at least 27 µM, at least 28 µM, at least 29 µM, at least 30 µM, at least 31 µM, at least 32 µM, at least 33 µM, at least 34 µM, at least 35 µM, at least 36 µM, at least 37 µM, at least 38 µM, at least 39 µM, at least 40 µM, at least 41 µM, at least 42 µM, at least 43 µM, at least 44 µM, at least 45 µM, at least 46 µM, at least 47 µM, at least 48 µM, at least 49 µM, at least 50 µM, at least 51 µM, at least 52 µM, at least 53 µM, at least 54 µM, at least 55 µM, at least 56 µM, at least 57 µM, at least 58 µM, at least 59 µM, at least 60 µM, at least 61 µM, at least 62 µM, at least 63 µM, at least 64 µM, at least 65 µM, at least 66 µM, at least 67 µM, at least 68 µM, at least 69 µM, at least 70 µM, at least 71 µM, at least 72 µM, at least 73 µM, at least 74 µM, at least 75 µM, at least 76 µM, at least 77 µM, at least 78 µM, at least 79 µM, at least 80 µM, at least 81 µM, at least 82 µM, at least 83 µM, at least 84 µM, at least 85 µM, at least 86 µM, at least 87 µM, at least 88 µM, at least 89 µM, at least 90 µM, at least 91 µM, at least 92 µM, at least 93 µM, at least 94 µM, at least 95 µM, at least 96 µM, at least 97 µM, at least 98 µM, or at least 99 µM. In one embodiment of all aspects, the concentration of the agent contacting the cell is more than 100 µM.

In one embodiment of all aspects, the cell is contacted by an agent in vivo, in vitro, or ex vivo. As used herein, "in vivo" refers to contacting a cell with an agent within a whole living animal, including humans and plants as opposed to a tissue extract or dead organism. As used herein, "in vitro" refers to contacting a cell with an agent outside its normal biological context, for example in a petri dish or tissue culture well. As used herein, "ex vivo" refers to contacting a cell with an agent external, or outside of its biological environment with minimal alterations to the cells natural conditions, for example an intact tissue extracted from an animal. Ex vivo conditions is a more controlled condition than that of an in vivo experiment.

In one embodiment of all aspects, the cell is a mammalian cell. In one embodiment of all aspects, the cell is a human cell. In one embodiment of all aspects, the cell is a non-human mammalian cell. Non-limiting examples of non-human mammals include primates, such as chimpanzees, cynomologous monkeys, spider monkeys, and macaques, e.g., Rhesus; rodents, such as mice, rats, woodchucks, ferrets, rabbits and hamsters; and domestic and game animals, such as cows, horses, pigs, deer, bison, buffalo, feline species, e.g., domestic cat, and canine species.

In one embodiment of all aspects, the HSC specification is maintained long-term. HSCs can refer to long term HSC (LT-HSC) and short term HSC (ST-HSC). A long term HSC typically includes the long term contribution to multi-lineage engraftment after transplantation.

A short term HSC is typically not multi-lineage. LT-HSC and ST-HSC are differentiated, for example, based on their cell surface marker expression. LT-HSC are CD34−, SCA-1+, Thy1.1+/lo, C-kit+, Lin−, CD135−, Slamf1/CD150+, whereas ST-HSC are CD34+, SCA-1+, Thy1.1+/lo, C-kit+, lin−, CD135−, Slamf1/CD150+, Mac-1 (CDlIb)lo ("lo" refers to low expression). In addition, ST-HSC are less quiescent (i.e., more active) and more proliferative than LT-HSC. LT-HSC have unlimited self-renewal (i.e., they survive throughout adulthood), whereas ST-HSC have limited self-renewal (i.e., they survive for only a limited period of time).

As used herein, "long term" refers to a period of time that is at least 3 months. In one embodiment, HSC specification is maintained for at least 3, 4, 5, 6, 7, 8, 9, 10, 11 or more months, at least 1, 2, 3, 4, 5, 6, 7, 8, 9, 10 or more years.

As used herein, "short term" refers to a period of time that is less than 3 months. In one embodiment, HSC specification is maintained for at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 days.

One aspect of the invention relates to a cell obtained using the methods for inducing HSC-specificity described herein. The cell obtained can be singular, or a population thereof. The cell obtained, or population thereof, can be isolated using standard techniques known in the art. The cell population thereof can be pure. Used in this context, "pure" refers to a population of cells substantially similar consisting of a single cell type. The cell population, in one embodiment can be mixed, including a HSC-induced cell and an at least second, different cell type.

HSC Transplantation

Transplantation of hematopoietic cells has become the treatment of choice for a variety of inherited or malignant diseases. The donor and the recipient can be a single individual or different individuals, for example, autologous or allogeneic transplants, respectively. When allogeneic transplantation is practiced, regimes for reducing implant rejection and/or graft vs. host disease, as well known in the art, should be undertaken. Such regimes are currently practiced in human therapy. The cell populations selected can also be depleted of T lymphocytes, which may be useful in the allogeneic and haploidentical transplants setting for reducing graft-versus-host disease.

Most advanced regimes are disclosed in publications, e.g., by Slavin S. et al., e.g., J Clin Immunol 2002; 22:64, and J Hematother Stem Cell Res 2002; 11:265, Gur H. et al. Blood 2002; 99:4174, and Martelli M F et al, Semin Hematol 2002; 39:48, which are incorporated herein by reference.

In one embodiment of all aspect, the methods described herein are used for preparing autologous hematopoietic cells for transplantation. Induced HSCs can be administered to a subject either locally or systemically. Methods for administering bone marrow transplants to a subject are known in the art and are described in medical textbooks, e.g., Whedon, M. B. (1991) Whedon, M. B. "Bone Marrow Transplantation: Principles, Practice, and Nursing Insights", Boston: Jones and Bartlett Publishers. Bone marrow cells from a healthy patient can be removed, preserved, and then replicated and re-infused should the patient develop an illness which either destroys the bone marrow directly or whose treatment adversely affects the marrow. If the patient is receiving his or her own cells, this is called an autologous transplant; such a transplant has little likelihood of rejection.

Exemplary methods of administering stem cells to a subject, particularly a human subject, include injection or transplantation of the cells into target sites in the subject. The induced HSCs can be inserted into a delivery device which facilitates introduction, by injection or transplantation, of the cells into the subject. Such delivery devices include tubes, e.g., catheters, for injecting cells and fluids into the body of a recipient subject. The tubes additionally have a needle, e.g., a syringe, through which the cells of the invention can be introduced into the subject at a desired location. The stem cells can be inserted into such a delivery device, e.g., a syringe, in different forms. For example, the cells can be suspended in a solution, or alternatively embedded in a support matrix when contained in such a delivery device.

As used herein, the term "solution" includes a pharmaceutically acceptable carrier or diluent in which the cells of the invention remain viable. Pharmaceutically acceptable carriers and diluents include saline, aqueous buffer solutions, solvents and/or dispersion media. The use of such carriers and diluents is known in the art. The solution is preferably sterile and fluid to the extent that easy syringability exists.

Preferably, the solution is stable under the conditions of manufacture and storage and preserved against the contaminating action of microorganisms such as bacteria and fungi through the use of, for example, parabens, chlorobu-tanol, phenol, ascorbic acid, thimerosal, and the like. Solutions of the invention can be prepared by incorporating stem cells as described herein in a pharmaceutically acceptable carrier or diluent and, as required, other ingredients enumerated above, followed by filtered sterilization.

In some embodiments of all aspects, the HSC differentiates into a blood cell following transplantation into a subject. In some embodiments of all aspects, the HSC is committed to the blood lineage following transplantation into a subject. Differentiation of HSCs to fully differentiated blood cells is believed to be an irreversible process under normal physiological conditions. Hematopoietic lineage specification takes place within the bounds of strict lineal relationships: for example, megakaryocyte progenitors give rise to megakaryocytes and ultimately platelets, but not to any other blood lineages. A HSC can differentiate into all blood cell types. Non-limiting examples of blood cells that a HSC can differentiate into include a myeloid progenitor, a lymphoid progenitor, a megakaroblast, a promegakarocyte, a megakaryocyte, a thrombocyte, a proerythroblast, a basophilic erythroblast, a polychromatic erythroblast, a orthochromatic erythroblast, a polychromatic erythrocyte, an erythrocyte, a myeloblast, a B. promyelocyte, a B. myelocyte, a B. metamyelocyte, a B. band, a Basophil, a N. promyelocyte, a N. myelocyte, a N. metamyelocyte, a N. band, a neutrophil, an E. promyelocyte, an E. myelocyte, an E. metamyelocyte, an E. band, an eosinophil, a monoblast, a promonocyte, a monocyte, a macrophage, a myeloid dendritic cell, a lymphoblast, a prolymphocyte, a small lymphocyte, a B lymphocyte, a T lymphocyte, a plasma cell, a large granular lymphocyte, and a lymphoid dendritic cell.

Increasing HSC Numbers

One aspect of the invention provides a method for increasing HSC in a subject comprising: administering an agent selected from the group consisting of Ro5-3335, SU-5402, sc-221405, and AI-10-49 to the subject.

In some embodiment of any of the aspects, the subject has or is at risk of having decreased blood cell levels compared to control blood cell levels, (e.g. blood or bone marrow disorder). In one embodiment any of the aspects, the subject has blood cell levels decreased at least 1% compared to control blood cell levels. In one embodiment any of the aspects, the subject has blood cell levels decreased at least 1%, 5%, 10%, 15%, 20%, 25%, 30%, 35%, 40%, 45%, 50%, 55%, 60%, 65%, 70%, 75%, 80%, 85%, 90%, 95%, 99% or more compared to control blood cell levels. A skilled clinician can determine if a subject has or is at risk of having decreased blood levels, for example by conducting a complete blood count (CBC) test. A CBC includes obtaining a blood sample from a subject using standard techniques and calculating the number of blood cells in a specified volume of sample. Blood cell levels are compared to control blood cell levels, which are defined at the average blood cell count for a healthy individual at a specific age and gender. For example, the normal red blood cell range for an adult male is 4.7 to 6.1 million cells per microliter (mcL), and 4.0 to 5.5 million mcL for a young male child. The blood cell count control may vary between clinicians and laboratories conducting the CBC.

Non-limiting diseases and disorders associated with a decrease in white blood cells include an infection, for example a viral infection, certain cancers, for example leukemia, and an autoimmune disorder that destroy white blood cells. Non-limiting diseases and disorders associated with a decrease in red blood cells include anemia, hemolysis, leukemia, multiple myeloma, and thyroid disorders. As used herein, a "thyroid disorder" refers to a disorder or condition that results in the increased or decreased function of the thyroid by either directly affecting the structure or function of the thyroid.

In some embodiment of any of the aspects, the subject has anemia or blood loss. Anemia is a condition defined by a deficiency in red blood cells or of hemoglobin in the blood compared to control red blood cell levels. Symptoms of anemia include, but are not limited to, fatigue, shortness of breath, dizziness, and rapid heartbeat. Anemia is diagnosed by a skilled clinician using a CBC, as described above.

In some embodiment of any of the aspects, the subject is a bone marrow donor. In some embodiment of any of the aspects, the subject has depleted bone marrow. Bone marrow is a spongy tissue that promotes the formation of blood cells. A decrease in bone marrow is associated with low blood levels and can result in the diseases and disorders associated with low blood as described herein. Diseases and disorders associated with a reduction in bone marrow (bone marrow failure) include, but are not limited to, aplastic anemia, myelodysplastic syndromes, and paroxysmal nocturnal hemoglobinuria. A skilled clinician can determine the levels of bone marrow in a subject by using standard diagnostic tests, for example aspiration and biopsy of bone marrow. Aspiration is done first to collect a small amount of bone marrow fluid through a needle. A biopsy test collects a small amount of bone marrow tissue through a larger needle. Optionally, a biopsy test is done at the same time as the aspiration test.

As used herein "blood or bone marrow disorder" refers to any disease or disorder resulting from a decrease in blood cells or bone marrow in a subject, and is not limiting to the diseases and disorders described herein. A blood or bone marrow disorder can be caused by external factors, such as cigarette smoking or poor diet, or genetic factors that predisposition a subject disease or disorder that negatively affects red and/or white blood cells or bone marrow.

Dosages Forms and Administration

The dosages of an agent that increases the number of HSC in a subject can be determined by one of ordinary skill in the art depending on the severity of disease, the age and weight of the patient, and other pharmacokinetic factors generally understood in the art. The interrelationship of dosages for animals of various sizes and species and humans based on mg/m$^3$ of surface area is described by E. J. Freireich et al., "Quantitative Comparison of Toxicity of Anticancer Agents in Mouse, Rat, Hamster, Dog, Monkey and Man," Cancer Chemother. Rep. 50: 219-244 (1966). Adjustments in the dosage regimen can be made to optimize the therapeutic response. Doses can be divided and administered on a daily basis or the dose can be reduced proportionally depending on the therapeutic situation.

The dosage range depends upon the potency, and includes amounts large enough to produce the desired effect, e.g., an increase in HSC numbers. The dosage should not be so large as to cause unacceptable adverse side effects. Generally, the dosage will vary with the type of agent (e.g., Ro5-335 and SU-5402), and with the age, and condition of the patient. The dosage can be determined by one of skill in the art and can also be adjusted by the individual physician in the event of any complication. Typically, the dosage will range from 0.001 mg/kg body weight to 5 g/kg body weight. In some embodiments, the dosage range is from 0.001 mg/kg body weight to 1 g/kg body weight, from 0.001 mg/kg body weight to 0.5 g/kg body weight, from 0.001 mg/kg body weight to 0.1 g/kg body weight, from 0.001 mg/kg body weight to 50 mg/kg body weight, from 0.001 mg/kg body weight to 25 mg/kg body weight, from 0.001 mg/kg body weight to 10 mg/kg body weight, from 0.001 mg/kg body weight to 5 mg/kg body weight, from 0.001 mg/kg body weight to 1 mg/kg body weight, from 0.001 mg/kg body weight to 0.1 mg/kg body weight, from 0.001 mg/kg body weight to 0.005 mg/kg body weight. Alternatively, in some embodiments the dosage range is from 0.1 g/kg body weight to 5 g/kg body weight, from 0.5 g/kg body weight to 5 g/kg body weight, from 1 g/kg body weight to 5 g/kg body weight, from 1.5 g/kg body weight to 5 g/kg body weight, from 2 g/kg body weight to 5 g/kg body weight, from 2.5 g/kg body weight to 5 g/kg body weight, from 3 g/kg body weight to 5 g/kg body weight, from 3.5 g/kg body weight to 5 g/kg body weight, from 4 g/kg body weight to 5 g/kg body weight, from 4.5 g/kg body weight to 5 g/kg body weight, from 4.8 g/kg body weight to 5 g/kg body weight. In some embodiments of any of the aspects, the dose range is from 5 µg/kg body weight to 30 µg/kg body weight. Alternatively, the dose range will be titrated to maintain serum levels between 5 µg/mL and 30 µg/mL.

These agents can be administered orally, and they can be administered in conventional pill or liquid form. If administered in pill form, they can be administered in conventional formulations with excipients, fillers, preservatives, and other typical ingredients used in pharmaceutical formations in pill form. Typically, the agents are administered in a conventional pharmaceutically acceptable formulation, typically including a carrier. Conventional pharmaceutically acceptable carriers known in the art can include alcohols, e.g., ethyl alcohol, serum proteins, human serum albumin, liposomes, buffers such as phosphates, water, sterile saline or other salts, electrolytes, glycerol, hydroxymethylcellulose, propylene glycol, polyethylene glycol, polyoxyethylenesorbitan, other surface active agents, vegetable oils, and conventional anti-bacterial or anti-fungal agents, such as parabens, chlorobutanol, phenol, sorbic acid, thimerosal, and the like. A pharmaceutically-acceptable carrier within the scope of the present invention meets industry standards for sterility, isotonicity, stability, and non-pyrogenicity.

The agent formulated for administration to a subject can also be in pill, tablet, or lozenge form as is known in the art, and can include excipients or other ingredients for greater stability or acceptability. For the tablets, the excipients can be inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc, along with the substance for autophagy modulation and other ingredients.

The agents can also be administered in liquid form in conventional formulations that can include preservatives, stabilizers, coloring, flavoring, and other generally accepted pharmaceutical ingredients. Typically, when the agents are administered in liquid form, they will be in aqueous solution. The aqueous solution can contain buffers, and can contain alcohols such as ethyl alcohol or other pharmaceutically tolerated compounds.

Alternatively, the agent can be administered by subcutaneous injection by one of several routes well known in the art. The agent can additionally be formulated for topical administration by one skilled in the art. The agent can be administered parenterally. The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection, intraosseous infusion, infusion and other injection or infusion techniques, without limitation. In a preferred embodiment, the agent is administered parenterally.

The agent can be administered to a subject once in a single dose. The agent can be administered from once per day to up to at least five times per day or more, depending on the severity of the disease, the total dosage to be administered, and the judgment of the treating physician. In some cases, the agent need not be administered on a daily basis, but can be administered every other day, every third day, or on other such schedules. However, it can be preferred to administer the agent daily.

In some embodiments of any of the aspects, the agents described herein are administered as a monotherapy, e.g., no other treatment is administered to the subject.

In some embodiments of any of the aspects, the agents described herein are administered in combination with additional agents or therapeutics. Administered "in combination," as used herein, means that two (or more) different treatments are delivered to the subject during the course of the subject's affliction with the disorder, e.g., the two or more treatments are delivered after the subject has been diagnosed with the disorder (e.g., that reduces the blood cell count in a subject) and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery." In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered. The agents described herein and the at least one additional therapy can be administered simultaneously, in the same or in separate compositions, or sequentially. For sequential administration, the agent described herein can be administered first, and the additional agent can be administered second, or the order of administration can be reversed. The agent and/or other therapeutic agents, procedures or modalities can be administered during periods of active disorder, or during a period of remission or less active disease. The agent can be administered before another treatment, concurrently with the treatment, post-treatment, or during remission of the disorder.

When administered in combination, the agent and the additional agent (e.g., second or third agent), or all, can be administered in an amount or dose that is higher, lower or the same as the amount or dosage of each agent used individually, e.g., as a monotherapy. In certain embodiments, the administered amount or dosage of the agent, the additional agent (e.g., second or third agent), or all, is lower (e.g., at least 20%, at least 30%, at least 40%, or at least 50%) than the amount or dosage of each agent used individually. In other embodiments, the amount or dosage of agent, the additional agent (e.g., second or third agent), or all, that results in a desired effect (e.g., increase of blood cell count) is lower (e.g., at least 20%, at least 30%, at least 40%, or at least 50% lower) than the amount or dosage of each agent individually required to achieve the same therapeutic effect.

Efficacy Measurement

The efficacy of an agent to increase HSC numbers in a subject can be determined by the skilled clinician. Increased HSC is shown to give rise to increased blood cell production. Diagnostic procedures described herein that assess blood cell counts can be used to determine the efficacy of a treatment. A treatment is considered "effective treatment," as the term is used herein, if any one or all of the signs or symptoms of, as but one example, dizziness, or other clinically accepted symptoms or markers of the decreased blood cells are improved or ameliorated, e.g., by at least 10% following treatment with a composition comprising an agent described herein. Efficacy can also be measured by failure of an individual to worsen as assessed by need for medical interventions (e.g., progression of anemia is halted or at least slowed). Methods of measuring these indicators are known to those of skill in the art and/or described herein. Example methods are described above. Treatment includes any treatment, for example of blood or bone marrow disorder in an individual or an animal (some non-limiting examples include a human, or a mammal) and includes: (1) inhibiting the blood or bone marrow disorder, e.g., arresting, or slowing symptoms of the blood or bone marrow disorder, for example dizziness caused by anemia; or (2) relieving the blood or bone marrow disorder, e.g., causing regression of symptoms, reducing the symptoms by at least 10%; and (3) preventing future blood or bone marrow disorder.

Effective amounts, toxicity, and therapeutic efficacy of an agent, e.g., for increasing HSC numbers in a subject, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dosage can vary depending upon the dosage form employed and the route of administration utilized. The dose ratio between toxic and therapeutic effects is the therapeutic index and can be expressed as the ratio $LD_{50}/ED_{50}$. Compositions and methods that exhibit large therapeutic indices are preferred. A therapeutically effective dose can be estimated initially from in vivo assays. Also, a dose can be formulated in animal models to achieve a circulating plasma concentration range that includes the $IC_{50}$ (i.e., the concentration of the active ingredient, which achieves a half-maximal inhibition of symptoms). Levels in plasma can be measured, for example, by high performance liquid chromatography or other appropriate technique. The effects of any particular dosage can be monitored by a suitable bioassay. The dosage can be determined by a physician and adjusted, as necessary, to suit observed effects of the treatment.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

EXAMPLES

Example 1

HSCs have been used clinically to reconstitute the bone marrow, but 30 to 40% of patients lack a matched donor marrow[1]. ESCs and iPSCs can be directed to differentiate in vitro into many types of cells for disease modeling, regenerative medicine, and drug screening[2]. However, it is not yet possible to generate HSCs in vitro from pluripotent sources. A zebrafish embryo culture approach provides a fast and robust system to establish new pathways that can be useful targets to differentiate cells derived from iPSCs. A chemical genetic screen for compounds that can promote runx1 cells in zebrafish blastomere cultures was performed by culturing immediately with chemicals and imaging two days later. The runx1-CBFβ inhibitor Ro5-3335 was identified as a strong inducer of Runx1:GFP+ cells in zebrafish embryos in vivo. Ro5-3335 increased the number of HSPCs from hemogenic endothelium derived from human iPSCs, and mouse transplants with human hemogenic endothelial cells treated with Ro5-3335 showed engraftment of myeloid cells at 6 weeks. The cross-species approach involving zebrafish and mammalian systems thus offers complementary methodologies to engineer HSCs for therapy and demonstrates that transient runx1-CBFβ inhibition enhances HSC specification.

Introduction

Supplies of HSCs are limited and unmatched transplants carry high risks of infection, donor rejection and graft-versus-host disease. 'Designer' HSCs would have the potential to provide an unlimited source of patient-specific HSCs for transplantation. Since the ground-breaking generation of iPSCs, attempts have been made to engineer HSCs from iPSCs and embryonic stem cells (ESCs) using transcription factor reprogramming. Other efforts have endeavored to alter cell fate by using transcription factors to convert more differentiated cell types into HSCs. These approaches mostly produce embryonic-like cells with short-term engraftment potential, which are unable to give rise to all blood cell lineages[3].

HSCs develop in several anatomical sites during zebrafish development: the aorta-gonad-mesonephros region (AGM), caudal hematopoietic tissue (CHT), kidney marrow, and thymus[4]. These sites are analogous to those in mammalian embryogenesis: the placenta, yolk sac, aorta-gonad-mesonephros region, fetal liver, and then the bone marrow at birth[5]. In mice, the fetal liver is seeded at E9.5-10.5 and after E12.5, it becomes the main organ of HSC expansion, peaking at E15.5-16.5 before declining; HSCs then colonize the bone marrow at E18. In zebrafish, runx1 and cmyb are required for HSC development and are expressed in the AGM at 36 hours post fertilization (hpf)[6,7]. HSCs can differentiate and generate the entire array of cells in the blood system while maintaining a self-renewing population[8].

HSCs express runx1, a key hematopoietic transcription factor that is required for EHT[9]. To facilitate studies of blood development, a transgenic zebrafish line Runx1:GFP was generated[10], which expresses the mouse stem cell-specific Runx1+23 enhancer[11] driving GFP and labels zebrafish HSCs in all sites of definitive hematopoiesis. The stem cell frequency in these GFP+ populations is 1-to-3 and 1-to-35 HSC-to-Runx1:GFP cells at 72 hpf and adulthood, respectively. HSC formation from hemogenic endothelium is dependent on a heterodimeric transcription factor composed of runx1 (a DNA-binding protein) and core binding factor β (CBFβ, its obligate non-DNA-binding partner), and these two proteins have been reported to have temporally distinct roles[12].

One approach to derive and maintain HSCs from pluripotent sources is guided by the principle that in vitro differentiation must recapitulate processes during embryonic development. In the embryo, the complex array of signals and cell-cell interactions that allow HSCs to migrate, colonize, and expand in the different sites are largely unknown[13]. Despite the important role of the niche interactions in regulating HSC homing and maintenance, much of the molecular knowledge comes from transplantation experiments in irradiated adult mice to assess HSC function[13].

There is a desire to reprogram pluripotent cells to become hematopoietic stem cells in an effort to provide an alternative source of stem cells despite the limited successes in accomplishing this goal, in large part because human iPSCs require 36 days for differentiation to blood cells[14]. This setting is not amenable to high-throughput chemical screening because drugs would have to be added at various points in the culture. To address these issues, image-based chemical screening using cultured zebrafish pluripotent cells establishes a system that can be used in a high-throughput fashion that takes advantage of zebrafish genetics and development[15].

zebrafish embryo culture system in which blood progenitors arise in two days was have developed, thereby allowing an excellent experimental model to test a number of factors and conditions in high-throughput fashion.

The genetic switches involved in zebrafish hematopoietic development are well known and highly conserved: in vivo time lapse imaging showed that sclfβ is expressed in some flk1 endothelial cells to become hemogenic endothelium, runx1 transforms these cells into HSCs, and sclα expression then maintains the budding HSCs, which go on to become the founders of the hematopoietic system[16]. The availability of these reporter lines provides an opportunity to identify chemical modulators that can enhance hematopoietic specification and maintenance.

Herein, serum-free conditions for the culture of runx1 transgenic zebrafish embryos to find inducers of HSPCs was established. A screen was performed using zebrafish embryo cell cultures for modulators of runx1, and identified Ro5-3335, a runx1-CBFβ inhibitor, as a strong enhancer of Runx1:GFP cells in culture. Ro5-3335 increased Runx1:GFP expression in the CHT of zebrafish in vivo, and enhanced the expansion of human iPSC-derived HSPCs. Ro5-3335 was also tested using human iPSC-derived hemogenic endothelial cells in mouse transplants, and observed myeloid engraftment. These findings indicate that transient runx1-CBFβ chemical inhibition causes runx1 accumulation to enhance HSPC induction from pluripotent sources.

Results
Zebrafish Chemical Genetic Screen Identifies Regulators of Runx1 Expression.

Figure 1C:
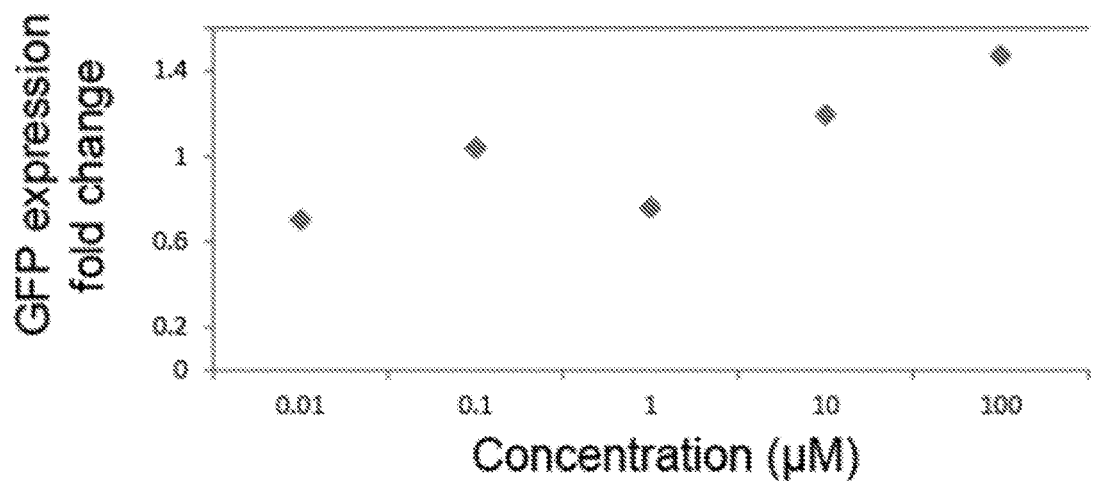
Figure 1D:
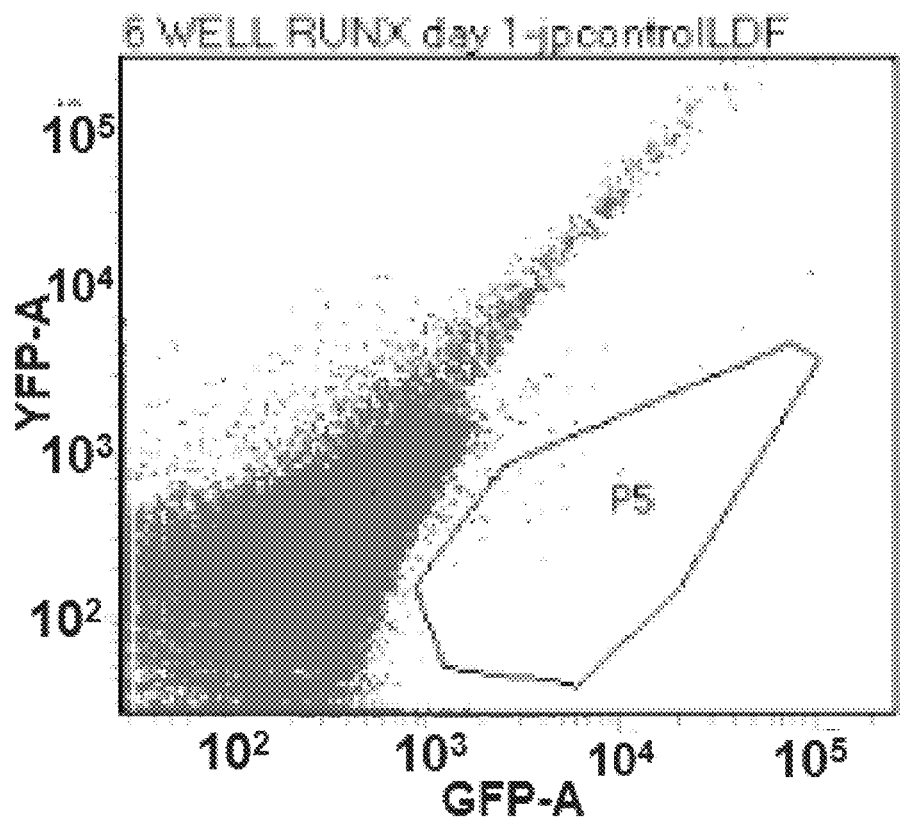
Figure 1D:
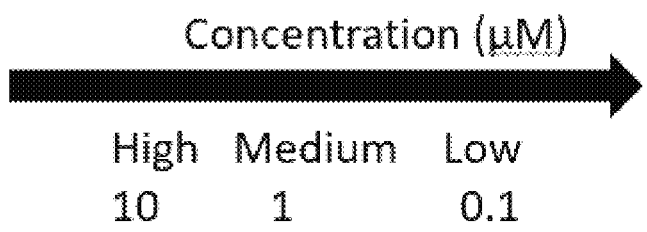

The chemical genetic screening approach that identified inducers of myogenesis[17] was adapted using a zebrafish embryo culture system to find modulators of runx1. 3,840 bioactive small molecules were screened in duplicate for inducers of Runx1:GFP, a marker of HSPCs[10] (FIG. 1A). 21 chemical hits were identified (0.54% hit rate, z-score >10) (Table 1). Among the hits obtained, it was observed that runx1-CBFβ inhibition increased Runx1:GFP fluorescence in the zebrafish embryo cultures in vitro (FIG. 1). Dose response studies were performed with several runx1-CBFβ inhibitor, including Ro5-3335, which were selected it for follow-up studies (FIG. 1C-D).

Ro5-3335 Increases Runx1:GFP Positive Cells In Vivo.

Figure 2A:
FIGS. 2A-2F show Ro5-3335 increases Runx1:GFP positive cells in vivo.
Figure 2B:
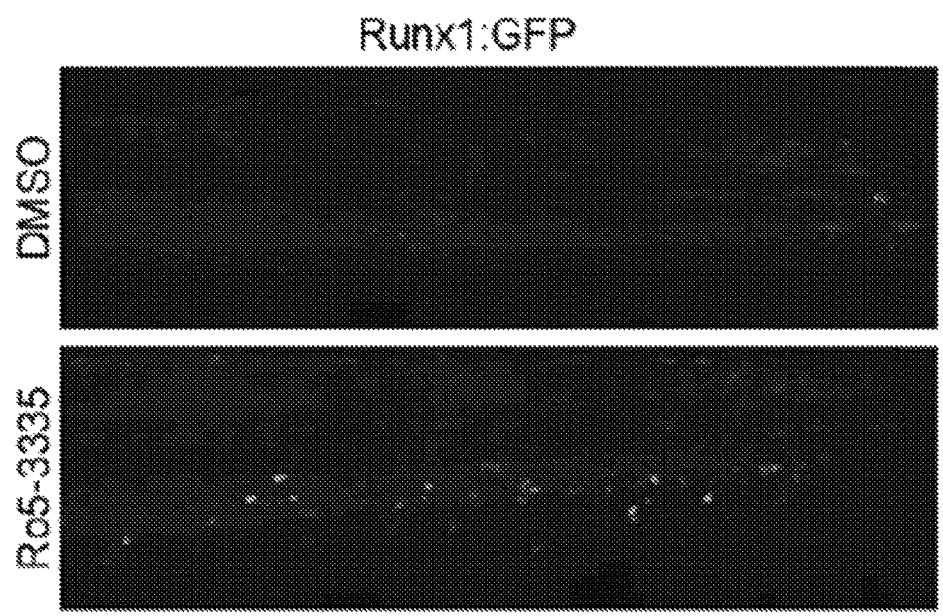
Figure 2C:
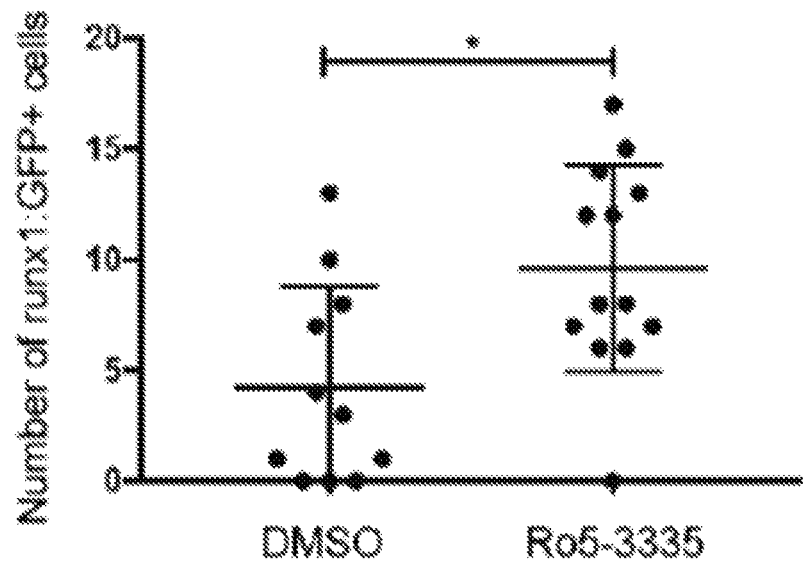
Figure 2D:
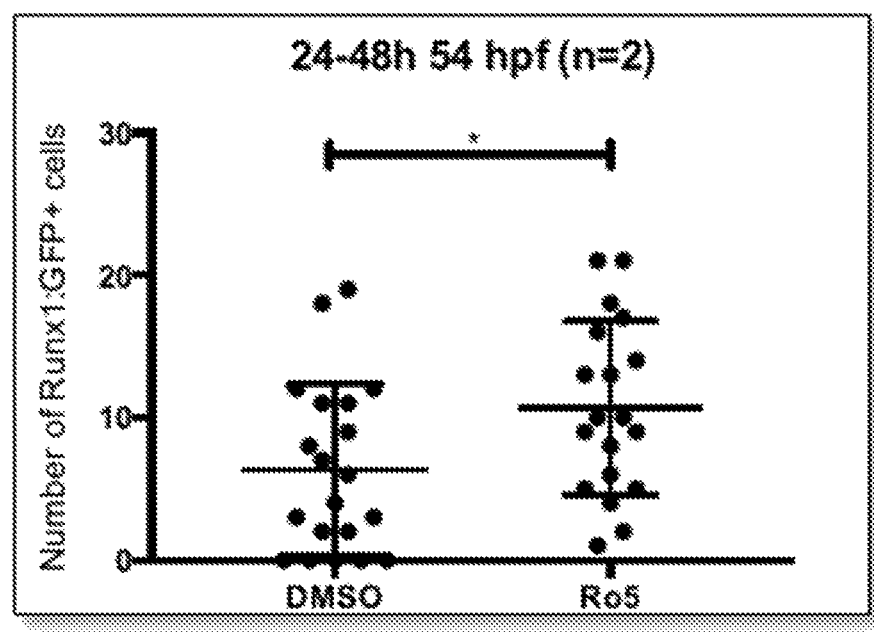
Figure 2E:
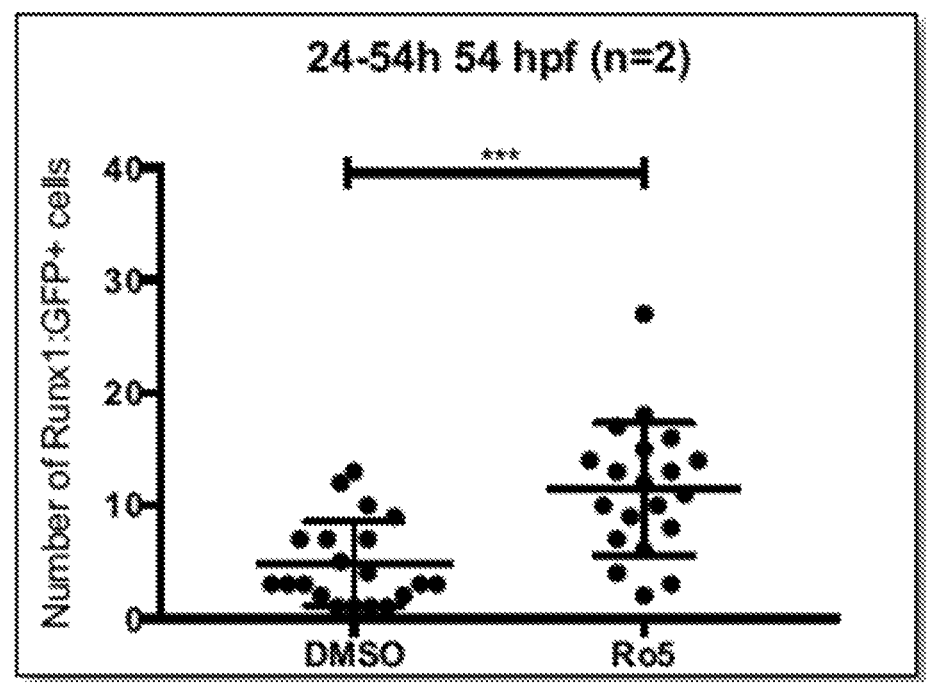
Figure 2F:
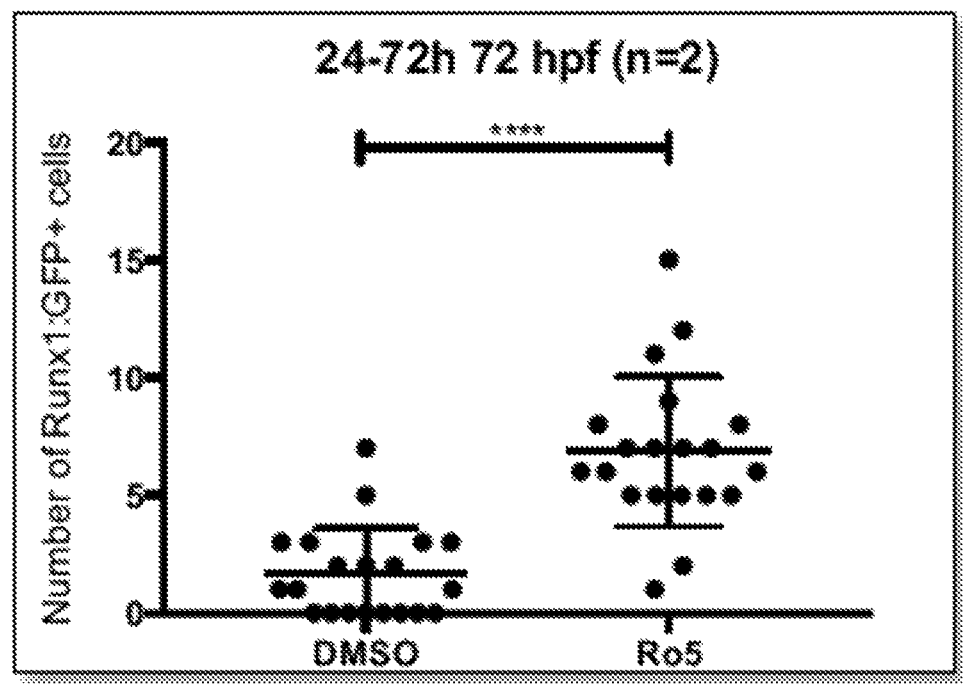

Runx1 is a transcription factor expressed in HSCs that is required for the emergence of definitive HSCs across species[6]. Thus, it was desirable to investigate if Ro5-3335 treatment functions on HSPCs. Transgenic zebrafish embryos were treated with Ro5-3335 between 24-30 hpf— before HSCs form and are released from the AGM—and quantified the number of Runx1:GFP+ cells in live embryos at 54 hpf located in the CHT (FIG. 2A). In embryos treated with Ro5-3335, a significant increase in the number of Runx1:GFP+ cells was observed (FIG. 2B-F). A significant difference at 72 hpf was not observed in the same embryos at 54 hpf from FIG. 2C (treated at 24-30 hpf), consistent with the notion that there are mechanisms that regulate the number of HSPCs in the developing embryo[18]. Based on these results, it was specifically speculated that runx1-CBFβ inhibitors potentially act by enhancing HSPC specification in the AGM, although other mechanisms are possible.

TABLE 1

Table 1. Chemical modulators of Runx1: GFP in zebrafish embryo cultures.

BI-D1870
5-methy1-2-(3-[methyl(pyridin-2-ylmethyl)amino]methyl)phenyl)-6-(trifluoromethyl)pyrimidin-4(3H)-one
2-(1-[1-(3,5,5-trimethylhexyl)piperidin-4-yl]-1H-1,2,3-triazol-4-yl)ethanol
2-(1-[1-(cycloheptylacetyl)piperidin-4-yl]-1H-1,2,3-triazol-4-yl)pyridine
2-(3-[(4-acetyl-1,4-diazepan-1-yl)methyl]phenyl)-3,5,6,7-tetrahydro-4H-cyclopenta[d]pyrimidin-4-one
2-[2-(azepan-1-ylmethyl)phenyl]-6-isobutylpyrimidin-4(3H)-one
SU 5402
RU 24969
Flupirtine maleate
NSC-95397
5-methyl-2-[3-(morpholin-4-ylmethyl)phenyl]-6-(trifluoromethyl)pyrimidin-4(3H)-one
Benzo[a]phenanthridine-10,11-diol, 5,6,6a,7,8,12b-hexahydro-, trans- [CAS]
4-Amino-1,8-naphthalimide
5,6-dimethyl-2-(3-[(4-phenylpiperazin-1-yl)methyl]phenyl)pyrimidin-4(3H)-one
6-butyl-2-(2-[(2-methylpyrrolidin-1-yl)methyl]phenyl)pyrimidin-4(3H)-one
5-methyl-2-[3-(thiomorpholin-4-ylmethyl)phenyl]-6-(trifluoromethyl)pyrimidin-4(3H)-one
2-(3-[(4-acetylpiperazin-1-yl)methyl]phenyl)-5-methyl-6-(trifluoromethyl)pyrimidin-4(3H)-one
Irinotecan HCl trihydrate
L-694,247
Manoalide
Doxorubicin The functional stem cell characteristics of Runx1:GFP positive cells derived in culture.

Figure 3A:
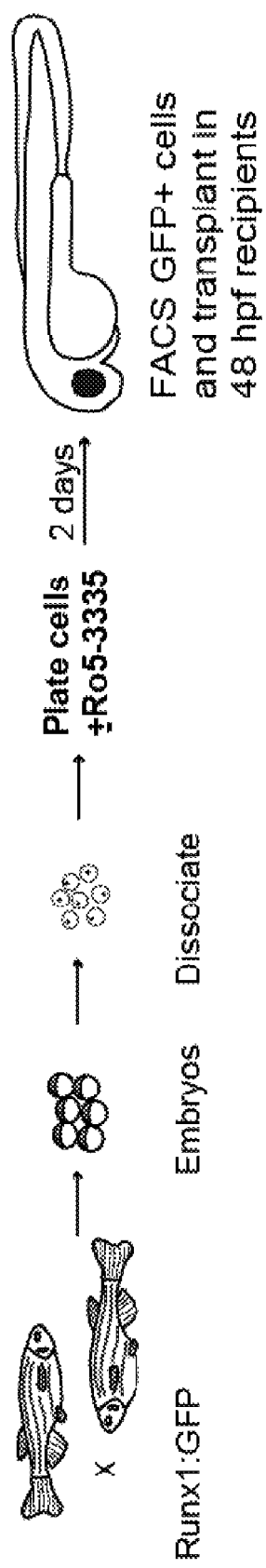
FIGS. 3A-3C show Ro5-3335 enhances Runx1:GFP chimerism in adult casper recipient fish.
Figure 3B:
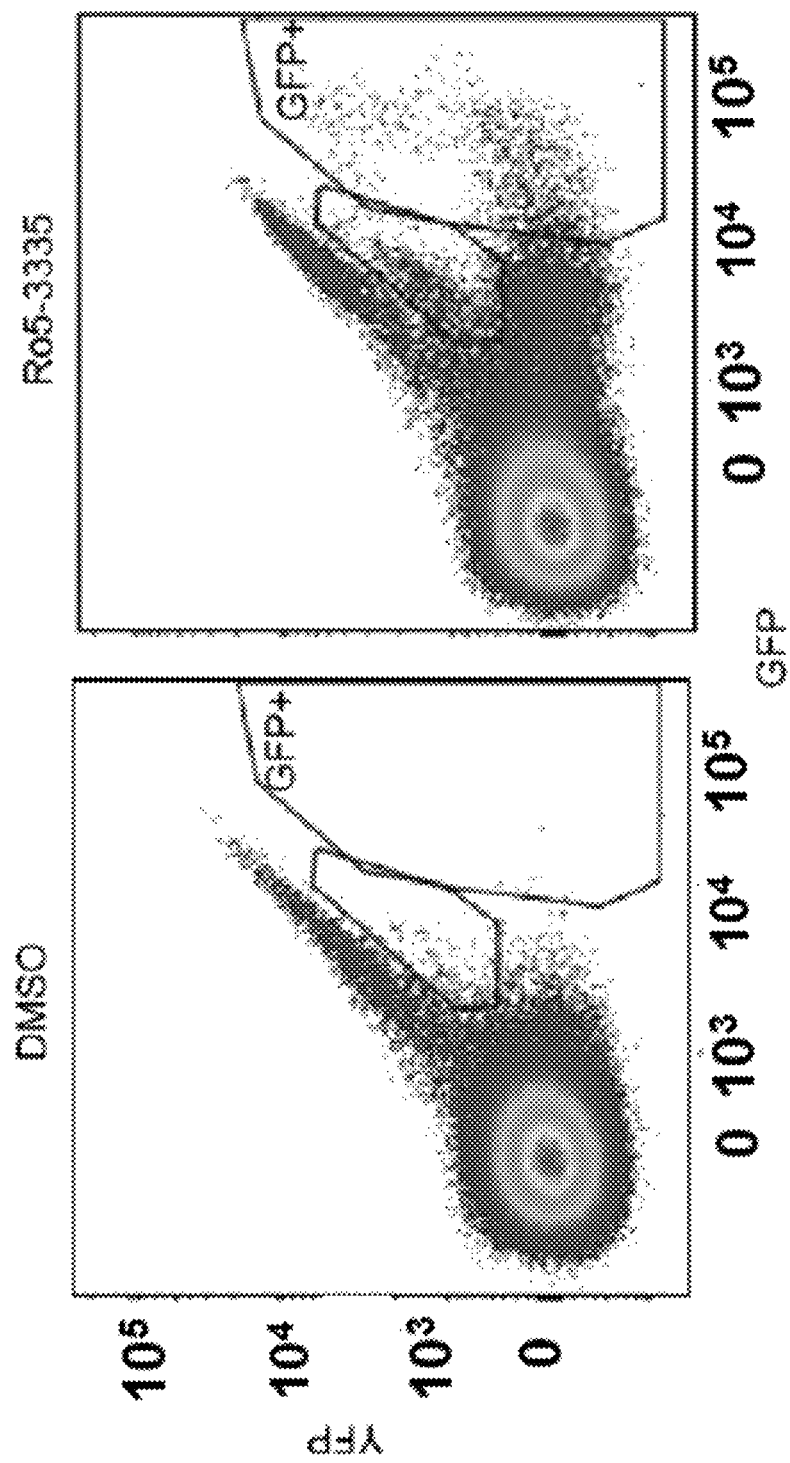
Figure 3C:
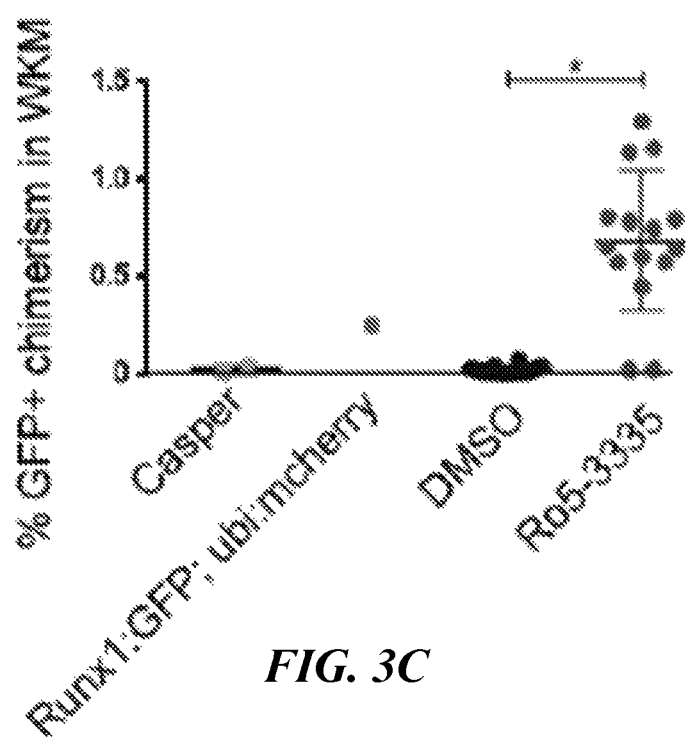

Multi-lineage reconstitution remains a sine qua non characteristic of transplantable HSCs[19]. To assess the in vivo hematopoietic functionality of the Runx1:GFP+ cells derived from the zebrafish embryo culture, cells into were transplanted prethymic 48 hpf casper embryos (FIG. 3A). It was estimated that each recipient received approximately 1-3 cells based on the calculations, and up to 20 GFP+ cells were observed in circulation three days post-transplant in the recipients, indicating that the cells derived in culture expanded in vivo. The recipient fish were grown to adulthood, and kidney marrow analysis showed enhanced GFP+ chimerism in the samples treated with the runx1-CBFβ inhibitor Ro5-3335 (FIG. 3B-C). The kidney marrow of two casper adult fish and one adult Runx1:GFP ubi:mCherry transgenic fish were used for comparison purposes as negative and positive controls, respectively. The significantly increased chimerism observed in recipients of Ro5-3335 treated cells indicates that runx1-CBFβ inhibition conferred an enhancement of HSPC engraftment or function immediately prior to transplant.

HSPC Expansion from Human Pluripotent Cells.

Figure 4A:
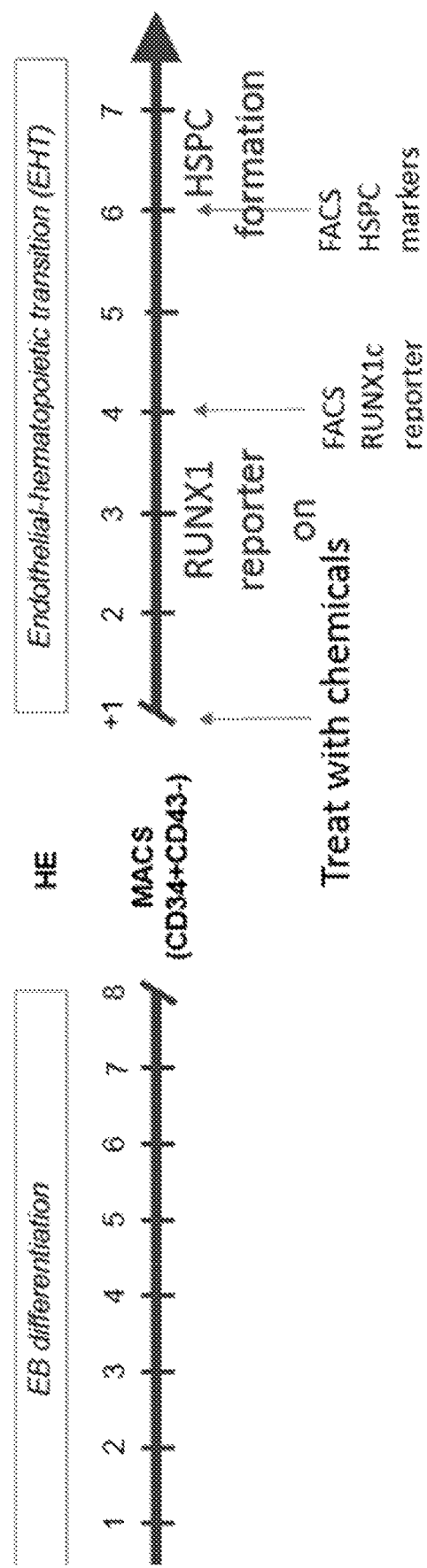
FIGS. 4A-4E show Ro5-3335 enhances human hematopoietic differentiation through hemogenic endothelium.
Figure 4B:
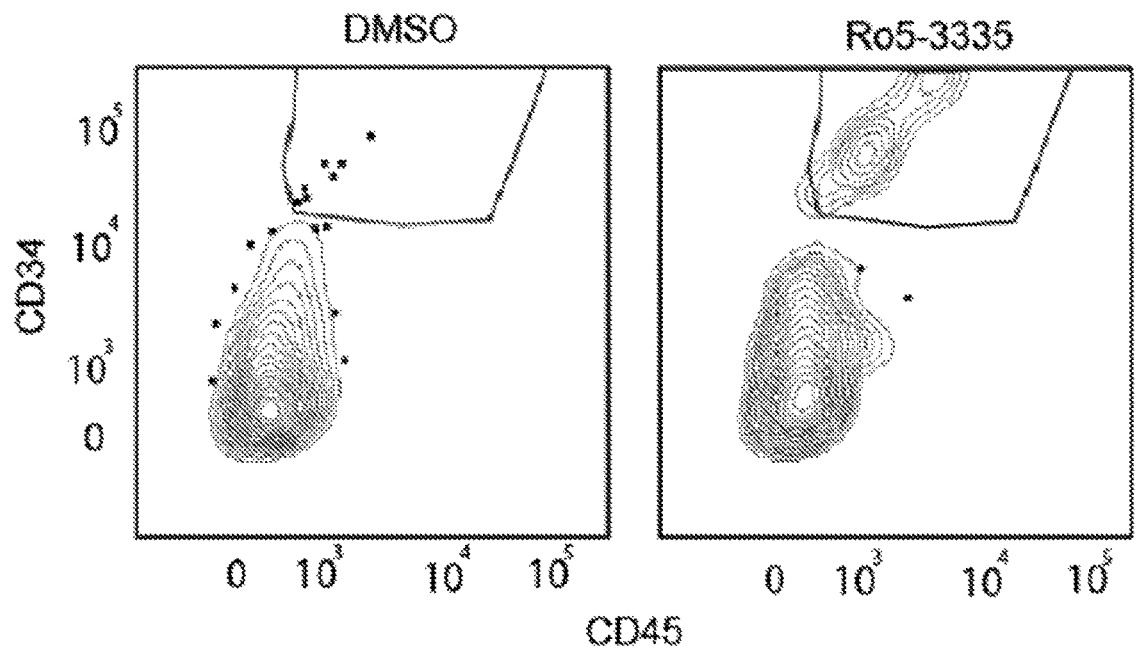
Figure 4C:
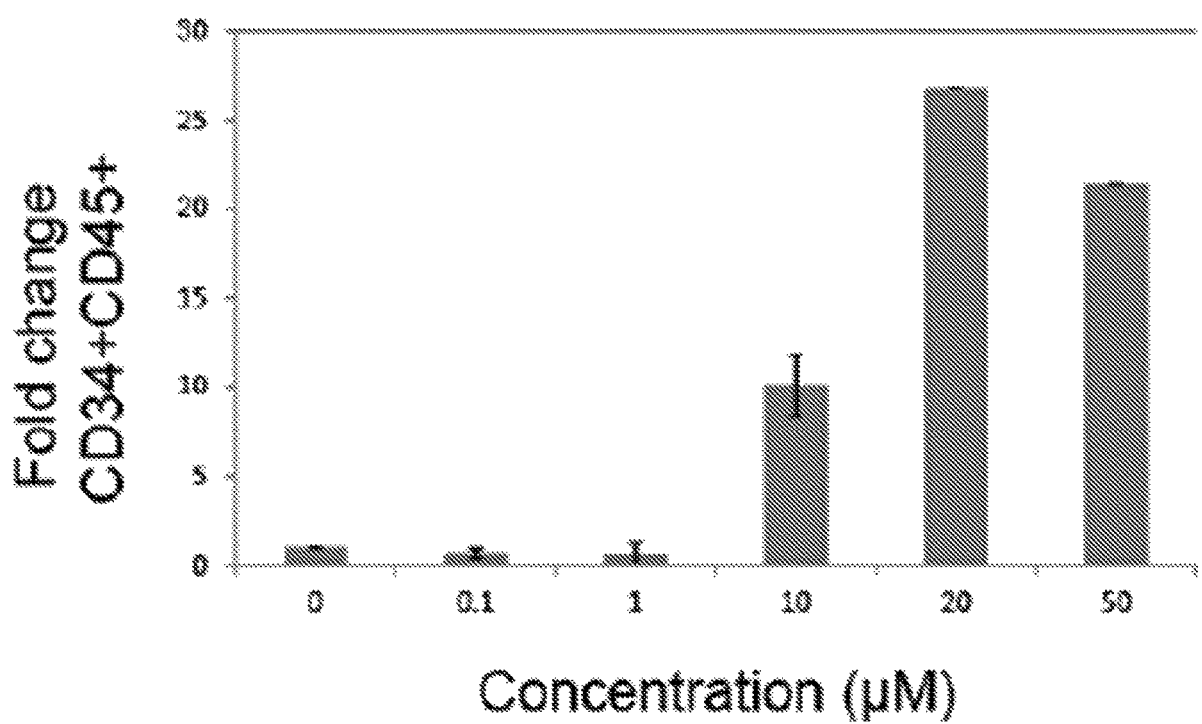
Figure 4D:
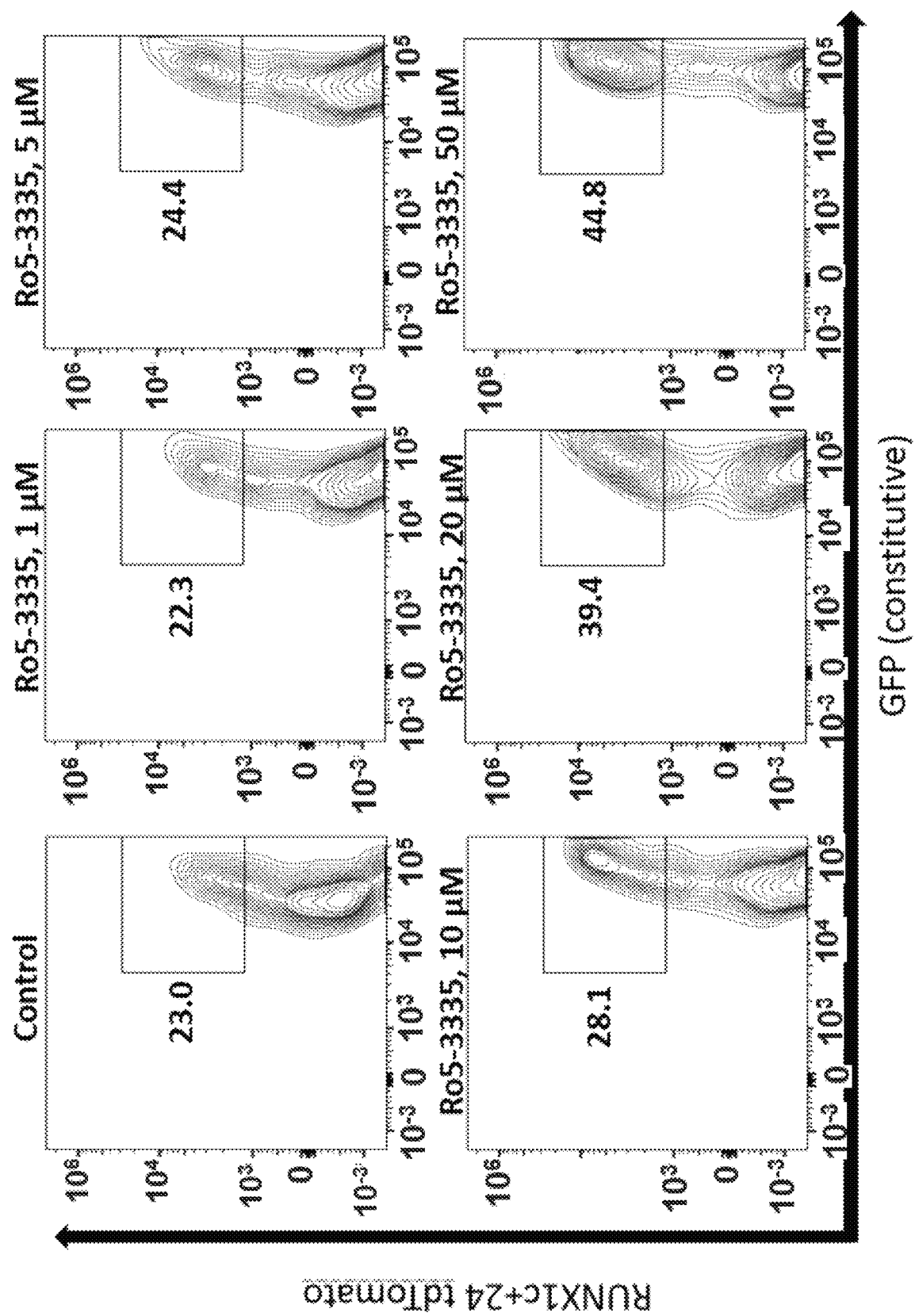
Figure 4E:
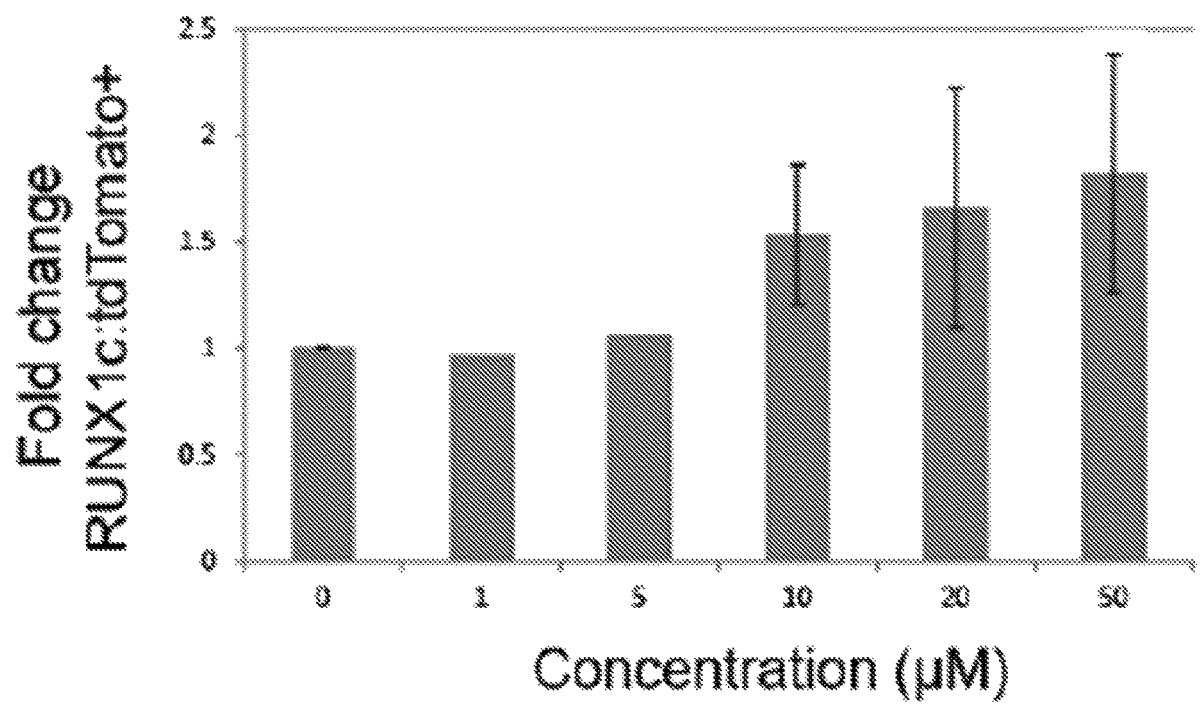

A protocol was used to produce hemogenic endothelium from human iPSCs[20] that seeks to model embryonic hematopoiesis whereby iPSC embryoid bodies are induced to form mesoderm and lead to the emergence of hematopoietic cells. In this system, CD34+FLK1+CD43− hemogenic endothelium cells are purified at day 8 of embryoid body formation and undergo EHT. These purified cells were treated with Ro5-3335, and observed a significant increase of CD34+CD45+ cells at day 6 of EHT (FIG. 4A-B). In addition, a dose-dependent effect with Ro5-3335 treatment was observed in cultures undergoing EHT using a RUNX1c-enhancer reporter cell line at day 4[21] (FIG. 4C). This RUNX1c:tdTomato reporter line is driven by the +24 intronic enhancer, which is required for hematopoietic specific expression, and was cloned into an iPSC line. Together, these results indicate that Ro5-3335 enhances the specification of HSPCs derived from pluripotent sources.

Figure 5A:
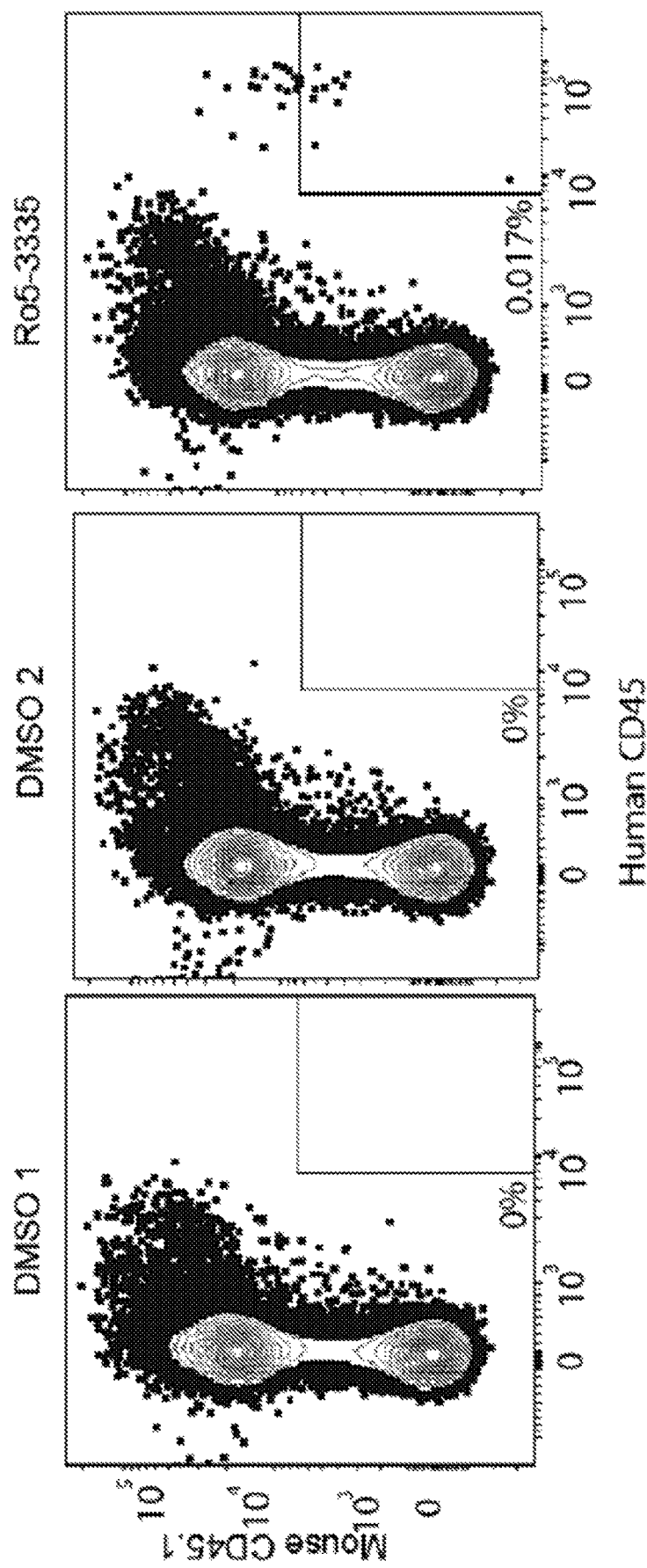
FIGS. 5A and 5B show engraftment of myeloid cells in mice injected with iPSC-derived human hemogenic endothelium cells.
Figure 5B:
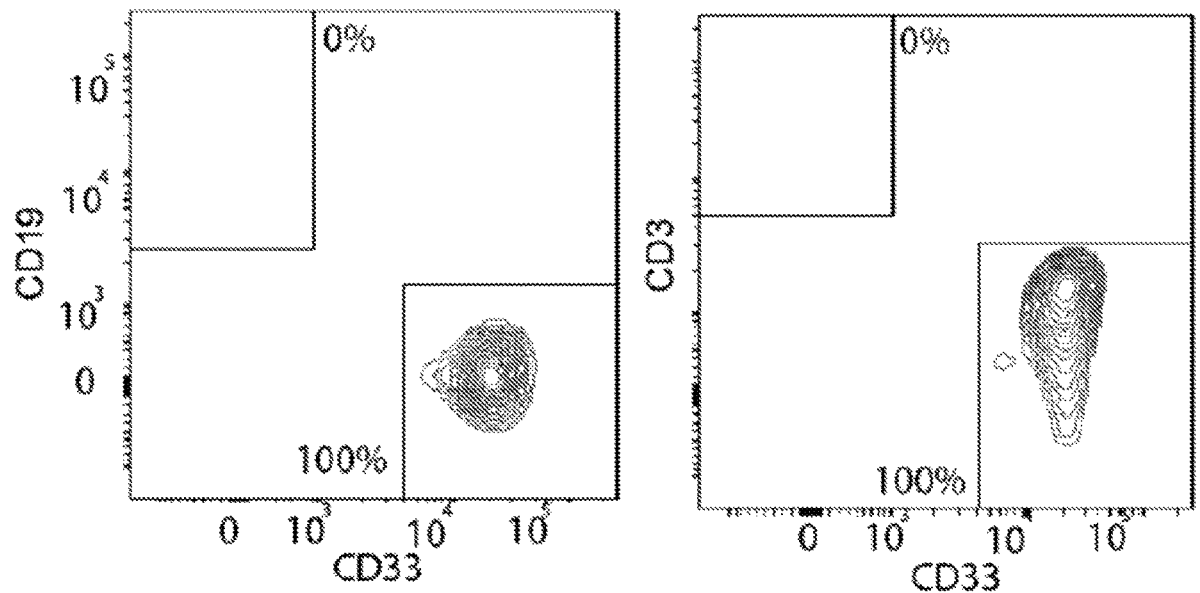

It was next sought to evaluate the self-renewal capacity and reconstitution potential of the HE cells in murine transplant settings following Ro5-3335 treatment. DMSO or Ro5-3335 treated cells were transplanted by intrafemoral injection in mice at day 4 of EHT. 6 weeks post-transplant, engraftment of myeloid cells in a mouse injected with Ro5-3335 treated cells was observed, and 0.017% chimerism of human CD45+ cells in the bone marrow was obtained (FIG. 5A). Although the chimerism was low, there was a clear population expressing the myeloid marker CD33 (FIG. 5B). B- and T-cells were not detected as expected after only 6 weeks post-transplant, which is too early for lymphoid cells to arise. There was no engraftment detected in the contralateral leg in this mouse. There was no engraftment from the DMSO treated cells as expected in the two mice that were analyzed thus far.

A model of runx1-CBFβ inhibition.

Figure 6A:
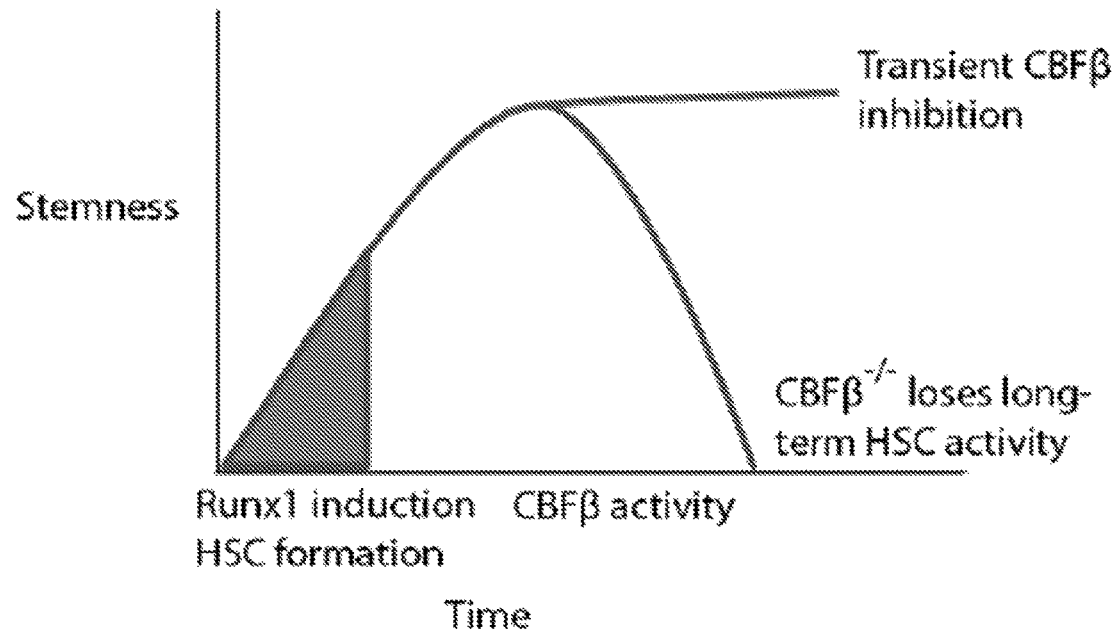
FIGS. 6A and 6B show a schematic of disruption of runx1 and CBFβ increases runx1 expressing cells in cultures.

To explain the results presented herein, one mechanism in which transient runx1-CBFβ chemical inhibition leads to the accumulation of runx1 was proposed (FIG. 6A). In cbfb$^{-/-}$ mutant zebrafish embryos, definitive hematopoiesis is impaired, and nascent HSPCs accumulate in the AGM and are not released[22]. Since runx1 is essential for HSC formation and deleting CBFB compromises long-term HSC function[12], chemical inhibition of this interaction is advantageous because it can be washed away for the treated cells to regain long-term HSC potential.

Figure 6B:
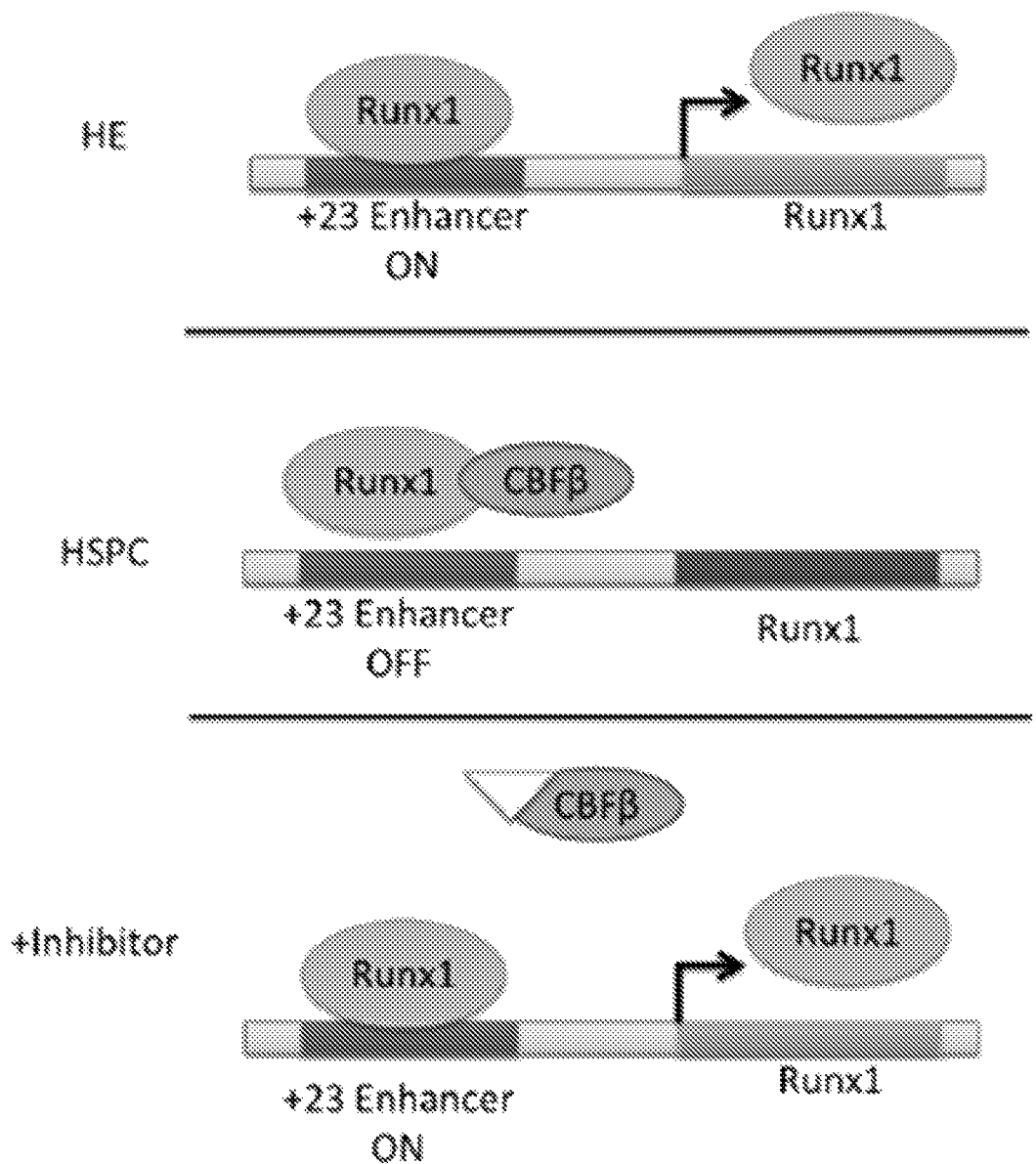

The model regarding the activity of Ro5-3335 relies on the Runx1+23 enhancer serving as a marker of HSPC activity (FIG. 6B). In the developing embryo, the enhancer element is bound by runx1 in HE cells, which increases runx1 expression. Whereas mutagenesis of the Runx1 binding site in the enhancer demonstrated it was not required for initial enhancer-driven expression, expression levels of hemogenic clusters were decreased at E10 of the dorsal aorta[23], indicates that Runx1 affects enhancer activity. The enhancer is thus responsive to runx1 activity and becomes activated in a CBFβ repressed state in the proposed model. Since the mouse Runx1+23 enhancer is bound by Gata2, Scl, Runx1, and Ets transcription factors[23], it is possible that runx1 is co-binding with Ets factors[24] at the enhancer. As HSPCs emerge, increasing CBFβ activity results in the enhancer element becoming turned off. In these cells, runx1 would then bind to other enhancer elements, such as those of myeloid genes that lead to cellular differentiation. However, treatment with Ro5-3335 disrupts the runx1-CBFβ interaction, enables the Runx1+23 enhancer to remain active, and maintains a stem cell state. Thus, runx1-CBFβ inhibition leads to increased Runx1:GFP expression.

Discussion

Through the chemical screening presented herein for modulators of runx1, factors that enhance HSPC specification from pluripotent sources were identified, including runx1-CBFβ inhibitors. The runx1-CBFβ inhibitor Ro5-3335 increased Runx1:GFP positive cells in the CHT of zebrafish embryos, and promoted the hematopoietic induction of CD34+CD45+ cells from human iPSCs. An HSC specification strategy using transient CBFβ inhibition was identified and proposed that washing off the inhibitor would allow the cells to continue developing normally and maintain long-term HSC activity after transplant. Chemical factors revealed in the zebrafish culture system thus establish pathways that can be useful targets to promote iPSC-derived HSC expansion, which would be transformative in regenerative medicine to aid in therapies of blood cell lineages and improve bone marrow transplant efficiencies.

When considering models of runx1-CBFβ inhibition, the inventors were intrigued by the resulting increase in Runx1: GFP+ cells in the CHT of live zebrafish embryos at 54 hpf following treatment of Ro5-3335 between 24-30 hpf Runx1-CBFβ inhibition may mimic a runx1 haploinsufficient state. Runx1 haploinsufficiency surprisingly conferred engraftment potential of E10 cells transplanted from the yolk sac of mice and appeared to cause a temporal shift in the appearance of HSCs[25]. Thus, one model that explains the observations consists of runx1-CBFβ inhibition acting to accelerate the onset of HSC development in the zebrafish AGM and thus resulting in an increase of Runx1:GFP+ cells at 54 hpf. Alternatively, runx1-CBFβ disruption may be acting on erythro-myeloid progenitors (EMPs).

Ro5-3335 has been reported as a direct RUNX1-CBFβ inhibitor[26], but elsewhere suggested to act as a SMARCA2 inhibitor[27], so it is contemplated that SMARCA2 inhibition also played a role in the effect observed on HSPC enhancement.

In the serum-free zebrafish embryo culture system, transgenic embryos are raised to the appropriate stage and dissociated into single cells. These cells are then plated with a chemical library and allowed to differentiate in vitro, and the fluorescence from the transgene is read out on a high-content imager. This approach facilitates rapid screening of thousands of small molecules and leverages the advantages of the zebrafish as a model system for chemical screening. The strength of this approach is particularly evident as the identification of Ro5-3335 as an inducer of Runx1:GFP was translated to mammalian hematopoietic systems successfully. It is noteworthy that the chemical genetic screening enabled the identification of the role of runx1-CBFβ, which would otherwise not have been possible by screening using a cbfb$^{-/-}$ genetic mutant that loses long-term HSPC function[22].

Materials and Methods

Culture of Dissociated Zebrafish Cells.

Stage-matched zebrafish embryos were dissociated at 24 hpf and grown in medium composed of 85% LDF medium, 5% FBS, and 10% embryo extract. LDF medium contains 50% Leibowitz's L-15 (Invitrogen), 20% DMEM (Invitrogen), and 30% DMEM/F-12 (Invitrogen), supplemented with 2% B27 (Gibco), 15 mM HEPES (Gibco), 1% L-glutamine (Gibco), 1% N2 (Gibco), 10 nM sodium selenite (Sigma), 0.018% sodium bicarbonate (Gibco), 0.04% Primocin (Invivogen), and 0.2% Penicillin-Streptomycin (Gibco). All zebrafish experiments and procedures were performed as per protocols approved by the Boston Children's Hospital IACUC.

High-Throughput Screen.

To screen each chemical library plate in duplicate, two 384-well plates were coated with 0.1% gelatin. Runx1: GFP[10] embryos at 24 hpf were washed with E3 embryo water and dechorionated with pronase. Embryos were washed with E3 embryo water, resuspended in blastomere media, mechanically homogenized, and filtered through a 40 m nylon mesh filter. Single cells obtained were aliquoted 40 μl per well at approximately 2 embryo equivalents per well, and immediately screened with chemicals from NIH (Evotec, 720), Library of Pharmacologically Active Compounds (Sigma, 1,440), ICCB Known Bioactives (Biomol, 480), and Nuclear Hormone Receptor and Kinacore (ChemBridge, 1,200) libraries at 30 μM. Cells were cultured in a 28° C. incubator with 5% $CO_2$ for 2 days. Cells were stained with DRAQ5™ (Cell Signaling Technology) and imaged using a CellVoyager™ 7000 (Yokogawa).

A 4× image of the nuclear and fluorescent expression from the entire well was then thresholded and percent area was computed using ImageJ/Fiji. Control wells (200 or more per plate) were identified using quartile exclusion of outliers, and using these wells, a standard curve was built with GFP vs. nuclear staining in MatLab. From that standard curve, residuals were calculated for each treated well and divided by the standard deviation in the control wells to obtain the z-score of each chemical treatment.

Dose response studies using zebrafish embryo cultures and follow-up experiments were performed with chemicals dissolved in DMSO.

Confocal Imaging.

Transgenic Runx1:GFP embryos from the same clutch were treated at the time points indicated (n>10 embryos per treatment group) with 5 µM Ro5-3335 diluted in E3. Live embryos were embedded in 0.8% low-melting point agarose containing 0.04 mg/mL Tricaine and imaged on a Nikon Eclipe Ti microscope with 20× Plan-Apo DIC N.A. 0.75. CHT cells were counted blindly in Z-stack image projections processed on Imaris software (Bitplane). The Runx1:GFP cell counts displayed in the graph.

Zebrafish Transplantation Studies.

Runx1:GFP ubi:mCherry embryos were dissociated at 24 hpf and plated with 50 µM Ro5-3335 or DMSO. After two days in culture, double-positive cells were sorted and transplanted into 48 hpf casper recipients as previously described[10]. The recipients were grown to adulthood and the whole kidney marrow was dissected at approximately 3 months and analyzed in an LSRII (BD Biosciences). As negative and positive controls, the kidney marrow of two casper adults and one Runx1:GFP ubi:mCherry adult were analyzed.

Human EHT Culture and Mouse Transplants.

Human iPSCs were cultured and differentiated into embryoid bodies as previously described[28]. At day 8 of embryoid body differentiation, HE cells were magnetically purified for EHT, and treated with DMSO or Ro5-3335. FACS analysis for CD34 and CD45 was performed at day 6 of EHT using an LSRFortessa™ (BD Biosciences). In the case of the RUNX1c-reporter cell line[21], RUNX1c activity was analyzed at day 4 of EHT using an LSR Fortessa (BD Biosciences).

Intrafemoral transplantations were performed as described previously[28]. NOD/LtSz-scidIL2Rgnull mice (Jackson Laboratory) were transplanted with approximately 100,000 HE cells at day 4 that were treated with 25 µM Ro5-3335 or DMSO. Due to the limited cell number that can be obtained during EHT, the transplants were performed over the course of several weeks.

Statistics.

P-values were determined by unpaired one-tailed t-test by comparing treated samples to untreated controls where appropriate. Statistics were performed using GraphPad Prism™ software.

REFERENCES

1 Gragert, L. et al. HLA match likelihoods for hematopoietic stem-cell grafts in the U.S. registry. *N Engl J Med* 371, 339-348, doi:10.1056/NEJMsa1311707 (2014).

2 Cohen, D. E. & Melton, D. Turning straw into gold: directing cell fate for regenerative medicine. *Nature reviews. Genetics* 12, 243-252, doi:10.1038/nrg2938 (2011).

3 Rowe, R. G., Mandelbaum, J., Zon, L. I. & Daley, G. Q. Engineering Hematopoietic Stem Cells: Lessons from Development. *Cell Stem Cell* 18, 707-720, doi:10.1016/j.stem.2016.05.016 (2016).

4 Orkin, S. H. & Zon, L. I. Hematopoiesis: an evolving paradigm for stem cell biology. *Cell* 132, 631-644, doi:10.1016/j.cell.2008.01.025 (2008).

5 Mikkola, H. K. & Orkin, S. H. The journey of developing hematopoietic stem cells. *Development* 133, 3733-3744, doi:10.1242/dev.02568 (2006).

6 North, T. E. et al. Runx1 expression marks long-term repopulating hematopoietic stem cells in the midgestation mouse embryo. *Immunity* 16, 661-672 (2002).

7 Mukouyama, Y. et al. Hematopoietic cells in cultures of the murine embryonic aorta-gonad-mesonephros region are induced by c-Myb. *Curr Biol* 9, 833-836 (1999).

8 Orkin, S. H. Diversification of haematopoietic stem cells to specific lineages. *Nature reviews. Genetics* 1, 57-64, doi:10.1038/35049577 (2000).

9 Chen, M. J., Yokomizo, T., Zeigler, B. M., Dzierzak, E. & Speck, N. A. Runx1 is required for the endothelial to haematopoietic cell transition but not thereafter. *Nature* 457, 887-891, doi:10.1038/nature07619 (2009).

10 Tamplin, O. J. et al. Hematopoietic stem cell arrival triggers dynamic remodeling of the perivascular niche. *Cell* 160, 241-252, doi:10.1016/j.cell.2014.12.032 (2015).

11 Bee, T. et al. The mouse Runx1+23 hematopoietic stem cell enhancer confers hematopoietic specificity to both Runx1 promoters. *Blood* 113, 5121-5124, doi:10.1182/blood-2008-12-193003 (2009).

12 Tober, J., Yzaguirre, A. D., Piwarzyk, E. & Speck, N. A. Distinct temporal requirements for Runx1 in hematopoietic progenitors and stem cells. *Development* 140, 3765-3776, doi:10.1242/dev.094961 (2013).

13 Ellis, S. J. & Tanentzapf, G. Integrin-mediated adhesion and stem-cell-niche interactions. *Cell and tissue research* 339, 121-130, doi:10.1007/s00441-009-0828-4 (2010).

14 Olivier, E., Qiu, C. & Bouhassira, E. E. Novel, high-yield red blood cell production methods from CD34-positive cells derived from human embryonic stem, yolk sac, fetal liver, cord blood, and peripheral blood. *Stem cells translational medicine* 1, 604-614, doi:10.5966/sctm.2012-0059 (2012).

15 Tamplin, O. J. et al. Small molecule screening in zebrafish: swimming in potential drug therapies. Wiley interdisciplinary reviews. *Developmental biology* 1, 459-468, doi:10.1002/wdev.37 (2012).

16 Zhen, F., Lan, Y., Yan, B., Zhang, W. & Wen, Z. Hemogenic endothelium specification and hematopoietic stem cell maintenance employ distinct Scl isoforms. *Development* 140, 3977-3985, doi:10.1242/dev.097071 (2013).

17 Xu, C. et al. A zebrafish embryo culture system defines factors that promote vertebrate myogenesis across species. *Cell* 155, 909-921, doi:10.1016/j.cell.2013.10.023 (2013).

18 Henninger, J. et al. Clonal fate mapping quantifies the number of haematopoietic stem cells that arise during development. *Nature cell biology* 19, 17-27, doi:10.1038/ncb3444 (2017).

19 Doulatov, S. & Daley, G. Q. Development. A stem cell perspective on cellular engineering. *Science* 342, 700-702, doi:10.1126/science.1238363 (2013).

20 Ditadi, A. et al. Human definitive haemogenic endothelium and arterial vascular endothelium represent distinct lineages. *Nature cell biology* 17, 580-591, doi:10.1038/ncb3161 (2015).

21 Ferrell, P. I., Xi, J., Ma, C., Adlakha, M. & Kaufman, D. S. The RUNX1+24 enhancer and P1 promoter identify a unique subpopulation of hematopoietic progenitor cells derived from human pluripotent stem cells. *Stem cells* 33, 1130-1141, doi:10.1002/stem.1940 (2015).

22 Bresciani, E. et al. CBFbeta and RUNX1 are required at 2 different steps during the development of hematopoietic stem cells in zebrafish. *Blood* 124, 70-78, doi:10.1182/blood-2013-10-531988 (2014).

23 Nottingham, W. T. et al. Runx1-mediated hematopoietic stem-cell emergence is controlled by a Gata/Ets/SCL-regulated enhancer. *Blood* 110, 4188-4197, doi:10.1182/blood-2007-07-100883 (2007).

24 Zhao, J. Y., Osipovich, O., Koues, O. I., Majumder, K. & Oltz, E. M. Activation of Mouse Tcrb: Uncoupling RUNX1 Function from Its Cooperative Binding with ETS1. *Journal of immunology* 199, 1131-1141, doi:10.4049/jimmunol.1700146 (2017).

25 Cai, Z. et al. Haploinsufficiency of AML1 affects the temporal and spatial generation of hematopoietic stem cells in the mouse embryo. *Immunity* 13, 423-431 (2000).

26 Cunningham, L. et al. Identification of benzodiazepine Ro5-3335 as an inhibitor of CBF leukemia through quantitative high throughput screen against RUNX1-CBFbeta interaction. *Proc Natl Acad Sci USA* 109, 14592-14597, doi:10.1073/pnas.1200037109 (2012).

27 Illendula, A. et al. Small Molecule Inhibitor of CBFbeta-RUNX Binding for RUNX Transcription Factor Driven Cancers. *EBioMedicine* 8, 117-131, doi:10.1016/j.ebiom.2016.04.032 (2016).

28 Sugimura, R. et al. Haematopoietic stem and progenitor cells from human pluripotent stem cells. *Nature* 545, 432-438, doi:10.1038/nature22370 (2017).

What is claimed is:

1. A method for inducing hematopoietic stem cell (HSC) specification in a cell, the method comprising;
   a) contacting a cell for a period of time with an agent selected from the group consisting of Ro5-3335, SU-5402, sc-221405, and AI-10; and
   b) removing said agent after said period of time, thereby inducing HSC specification in the cell,
   wherein the cell is selected from the group consisting of an hemogenic endothelial (HE) cell, an embryonic cell, an embryonic stem cell (ESC), a cell from a dissociated embryo, a cell from a dissociated embryo that is at least 9-hours post fertilization, an embryoid bodies, an induced pluripotent stem cell (iPSC), an aorta-gonad-mesonephros (AGM) cell, a placenta stem cell, an adult stem cell, and an amniotic stem cell,
   wherein the concentration of the agent is greater than 2 µM.

2. The method of claim 1, wherein the contacting is in vitro, ex vivo or in vivo.

3. The method of claim 2, wherein the contacting is in vitro.

4. The method of claim 1, wherein the period of time is between 1 and 6 days.

5. The method of claim 1, wherein the cell is a mammalian cell, human cell, or non-human mammalian cell.

6. The method of claim 1, wherein the cell of (a) is an isolated cell.

7. The method of claim 1, wherein the cell of (a) is an iPS cell.

8. The method of claim 1, wherein the cell of (a) is a human cell.

9. The method of claim 1, wherein HSC specification is maintained long-term.

10. The method of claim 9, wherein long-term is at least 3 months.

11. The method of claim 1, wherein the HSC specification-induced cell is transplanted into a recipient.

12. The method of claim 1, wherein the HSC specification induced cell differentiates into a blood cell.

\* \* \* \* \*